United States Patent
Ko et al.

(10) Patent No.: US 10,632,169 B2
(45) Date of Patent: Apr. 28, 2020

(54) METHODS OF USING GM604 IN MODULATING ALS DISEASE BIOMARKERS LEADING TO PROGNOSIS AND THERAPEUTIC TREATMENT FOR ALS DISEASE

(71) Applicant: Genervon Biopharmaceuticals, LLC, Pasadena, CA (US)

(72) Inventors: Pui-Yuk Dorothy Ko, Monterey Park, CA (US); William R. Swindell, Athens, OH (US)

(73) Assignee: Genervon Biopharmaceuticals, LLC, Pasadena, CA (US)

( * ) Notice: Subject to any disclaimer, the term of this patent is extended or adjusted under 35 U.S.C. 154(b) by 44 days.

(21) Appl. No.: 15/374,950

(22) Filed: Dec. 9, 2016

(65) Prior Publication Data

US 2017/0157197 A1 Jun. 8, 2017

Related U.S. Application Data

(63) Continuation-in-part of application No. PCT/US2016/039007, filed on Jun. 23, 2016.

(60) Provisional application No. 62/185,278, filed on Jun. 26, 2015.

(51) Int. Cl.
| | |
|---|---|
| A61K 38/08 | (2019.01) |
| G01N 33/68 | (2006.01) |
| C12Q 1/68 | (2018.01) |
| C12Q 1/6883 | (2018.01) |

(52) U.S. Cl.
CPC ............ *A61K 38/08* (2013.01); *C12Q 1/6883* (2013.01); *G01N 33/6896* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,309,877 B1 | 10/2001 | Chau et al. |
| 6,759,389 B1 | 7/2004 | Chau et al. |
| 6,841,531 B2 | 1/2005 | Chau et al. |
| 7,183,373 B2 | 2/2007 | Chau et al. |
| 7,507,713 B2 | 3/2009 | Chau et al. |
| 7,795,215 B2 | 9/2010 | Chau et al. |
| 8,673,852 B2 | 3/2014 | Ko et al. |
| 8,846,615 B2 | 9/2014 | Ko et al. |
| 8,986,676 B2 | 3/2015 | Deshpande et al. |
| 2013/0059757 A1* | 3/2013 | Gitler ............. C12Q 1/6883 506/10 |

FOREIGN PATENT DOCUMENTS

| | | | |
|---|---|---|---|
| WO | WO-02072822 A2 * | 9/2002 | ......... C07K 14/4702 |
| WO | WO2003044175 | 5/2003 | |
| WO | WO2004065410 | 8/2004 | |
| WO | WO2007058982 | 5/2007 | |
| WO | WO2008057609 | 5/2008 | |
| WO | WO2009105780 | 8/2009 | |
| WO | WO2016210123 | 12/2016 | |

OTHER PUBLICATIONS (Hope Now for ALS) GM604 ALS Phase IIa Trial Showed Lower TOP 43 [online], Feb. 2015. Retrieved from the Internet: : <URL: https://www.youtube.com/watch?v=uVZFQIrn8A4>; time stamps 0:07, 0:17; 1:05, 1:32.*
Clinical Trials.Gov: Archive: NCT01854294 on Feb. 11, 2014 [online]. U.S. National Institute or Health. Feb. 11, 2014 (retrieved on Oct. 3, 2016). Retrieved from the Internet: <URL: https:l/clinicaltrials.gov/archive/NCT01854294/2014_02_11>; pp. 1-8.
Ling, SC et al. Converging Mechanisms in ALS and FTO: Disrupted RNA and Protein Homeostasis. Neuron. Aug. 7, 2013; vol. 79, No. 3; pp. 1-47; p. 22. paragraphs 2-3; 001: 10.1016/j.neuron.2013.07. 033.
International Search Report for related International Application PCT/US10/039007 (WO2016210123 Published Dec. 29, 2016).

* cited by examiner

Primary Examiner — Robert C Hayes
(74) Attorney, Agent, or Firm — Karen S. Canady; canady + lortz LLP

(57) ABSTRACT

Biomarkers are not as commonly used in ALS drug development as in the drug development process for oncology. Biomarkers are important component of the ALS drug development pathway to demonstrate drug effect and target engagement. In a recent Phase 2A double-blind, randomized, placebo controlled clinical trial with GM604 (AKA MNTF, GM6), where ALS patients were treated with six doses of GM604 for two weeks and then continued to be evaluated for disease progression until 10 weeks after cessation of GM604 treatment, it was demonstrated that GM604 can modulate expression of ALS disease related genes, through pathways that bring about homeostasis of pertinent ALS biomarkers. The statistical significance in biomarker changes also correlate with treatment effects in clinical observations. This correlation of disease progression with the modulation of the biomarkers suggest that GM604 can be used effectively in modulating ALS disease biomarkers, and consequently can be used for prognosis of ALS disease progression and therapeutic treatment to slow down ALS disease progression. The biomarker modulation can be a measure of drug efficacy.

18 Claims, 8 Drawing Sheets
Specification includes a Sequence Listing.

Plasma TDP 43 vs. Time through Week 12

Plasma TDP-43 percent change versus baseline level

Plasma total Tau percent change versus baseline level

Plasma total SOD1 percent change versus baseline level

Gene Ontology (GO) analyses for GM6 regulated genes.

Genes associated with ALS in GWAS studies and their response to GM6 in SH-SY5Y cells.

SOD1 protein in CSF and plasma of GM6- and control-treated patients (Phase 2A clinical trial).

Functional associations of ALS-associated genes altered by GM6

SEQUENCE LISTING

```
<160> NUMBER OF SEQ ID NOS: 3

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Ser Arg Tyr Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Met Leu Ser Ala Phe Ser
1               5
```

METHODS OF USING GM604 IN MODULATING ALS DISEASE BIOMARKERS LEADING TO PROGNOSIS AND THERAPEUTIC TREATMENT FOR ALS DISEASE

RELATED APPLICATIONS

This Application takes priority from international application PCT/US16/39007 filed Jun. 23, 2016 entitled 'Methods of using GM604 in modulating ALS disease biomarkers leading to prognosis and therapeutic treatment for ALS disease', by Pui-Yuk Dorothy Ko, and U.S. Ser. No. 62/185,278, filed Jun. 25, 2015 by Pui-Yuk Dorothy Ko and entitled the same, both incorporated by reference in their entirety.

SEQUENCE LISTING

The instant application contains a Sequence Listing which has been submitted electronically in ASCII format and is hereby incorporated by reference in its entirety. Said ASCII copy, created on Feb. 8, 2017, is named GNV-010-CIP_SL.txt and is 1,267 bytes in size.

FIELD

The field includes modulation of ALS biomarkers to homeostasis by GM604 (GM6), the correlation with prognosis of ALS disease progression, and the correlation with therapeutic effect on ALS disease progression.

BACKGROUND

The following includes-information that may be useful in understanding the present inventions. It is not an admission that any of the information provided herein is prior art, or relevant, to the presently described or claimed inventions, or that any publication or document that is specifically or implicitly referenced is prior art.

Amyotrophic lateral sclerosis (ALS) is a progressive neurodegenerative disease. It affects the neurons in the brain and the spinal cord. Motor neurons reach from the brain to the spinal cord and from the spinal cord to the muscles throughout the body. When the motor neuron dies, the ability of the brain to initiate and control muscle movement is lost. The name Amyotrophic lateral sclerosis means when the muscle ("Myo") does not ("A") receive nourishment ("Trophic"), the muscles "atrophies" or wastes away. This leads to the local area ("lateral") of muscles where portion of the nerve cells signal and control the muscles degenerates and leads to scarring or hardening ("sclerosis") in the local area. As ALS disease progresses, people lose the ability to speak, cat, move and breathe. The motor neurons that provide voluntary movements and muscle control dies. In the ALS patient's own words, they are watching themselves dying off a little each day, trapped in a body that cannot move.

Amyotrophic Lateral Sclerosis (ALS, also known since the late 1930s as Lou Gehrig's Disease, and also known as motor neuron disease in other countries) is a uniformly-fatal neurodegenerative disease in which the neurons controlling the voluntary skeletal muscles wither and die. This renders the patient progressively paralyzed until respiratory failure finally ends life. The average survival from diagnosis is between 2-5 years. The disease was first described in medical literature by Jean-Martin Charcot in 1869 and 145 years later there is still no truly-effective treatment for this savage disease (Xiong Z Q et al. 2002, Fas(t) balls and Lou Gehrig disease. A clue to selective vulnerability of motor neurons? Neuron. 12: 35 (6): 1011-1013).

ALS was for approximately 100 years thought to be a cell-autonomous disease in which some intrinsic failing of the motor neurons alone caused their death. Since the turn of last century, after discovery of the first genetic cause and subsequent development of the transgenic rodent model, the disease has been realized to be non-cell-autonomous. In fact, it is now understood that multiple cellular and support systems are involved in the development and progression of ALS. (Ilieva H, et al. 2009. Non-cell autonomous toxicity in neurodegenerative disorders: ALS and Beyond. J Cell Biol. 187:761-772.). Addressing only a single pathway is therefore unlikely to produce enough benefit to successfully treat a multi-factor disease.

Most drug actions are single targeted by either increasing the desired target (agonist) or decreasing the undesirable target (antagonist). For example, if the over expression of X causes certain disease, the drug can be an antibody binding to X to decrease its presence.

Central Nervous system diseases are very complex and involve more than a single disease pathway or a single target. What is needed is a high level upstream master regulator which is active and functional in the nervous system development at the embryonic stage, one that may provide multi-targeted therapeutic effect. The invention satisfies this need. An MNTF analog GM604 was shown to have therapeutic effect through modulating multi-targets is an aspect of the invention. GM604 is the name assigned for ALS therapeutic treatment. GM602 is assigned for ischemic stroke treatment. GM608 is assigned for Parkinsonigned for treatment.

BRIEF SUMMARY

The inventions described and claimed herein have many attributes and embodiments including, but not limited to, those set forth or described or referenced in this Summary. The inventions described and claimed herein are not limited to or by the features or embodiments identified in this Summary, which is included for purposes of illustration only and not restriction.

These and other aspects and embodiments of the inventions described and claimed herein will be apparent from and throughout the application and claims, all of which shall be considered to be a part of the written description thereof.

In one aspect, the invention is directed toward methods of monitoring, prognosing, and treating ALS.

Accordingly, in one embodiment a method of monitoring ALS is provided where GM604 is administered to a subject to regulate at least one of the following biomarkers: TDP-43, SOD1, and Tau. The regulation of these biomarkers is monitored after administration of GM604, and a known parameter associated with ALS disease progression is measured to make an evaluation of ALS disease progression. Then, a determination is made as to whether the regulation of the biomarker correlates with an ALS disease progression determination.

In another embodiment, a method of prognosis for ALS is provided where GM604 is administered to a subject to regulate at least one of the following biomarkers: TDP-43, SOD1, and Tau. The regulation of these biomarkers is monitored after administration of GM604, and a known parameter associated with ALS disease progression is measured to make an evaluation of ALS disease progression.

Then, a determination is made as to whether the biomarker predicts the ALS disease progression determination.

In another embodiment, a method of regulating biomarkers in a subject is provided. In this embodiment, a candidate subject for administration of GM604 is selected. The GM604 is administered to the subject in a preselected amount to the subject where the administration regulates at least one of the following biomarkers: TDP-43, SOD1, and Tau.

A method of treating ALS is also provided. In one embodiment, the method is carried out by administering GM604 to a subject to regulate at least one of the following biomarkers: TDP-43, SOD1, and Tau. The regulation of the biomarkers (activity and/or expression) is monitored and observed, and then an observation is made to determine whether the regulation of the biomarker correlates with ALS disease progression. In addition to the three biomarkers TDP-43, SOD1, and Tau, additional biomarkers such as Cystatin-C, IRS1, IRS2. AKT1, PIK3, and C9orf72 can be monitored. In certain preferred embodiments, at least one biomarker is regulated. In other embodiments, two or more biomarkers are regulated.

In another aspect, administration of GM604 results in a homeostasis of one or more biomarker. In another aspect, administration of GM604 results in a down regulation of one or more biomarker. In another aspect, administration of GM604 results in an up regulation of one or more biomarker.

BRIEF DESCRIPTION OF THE DRAWINGS

FIG. 1. shows Plasma TDP 43 vs. Time through Week 12. The Y-axis represents the percentage change from baseline, where the mean of percentage change in a group is the mean of the percentage changes in each subject of that group. Shown on the X-axis are time points in weeks, including at 0, 2, 4, 6, 8, 10, 12 weeks. The triangles in the plots represent the placebo and the circles represent subjects with GM604 treatment. The dotted line represents the slope of subjects treated with placebo, while the solid line represents the slope of subjects treated with GM604. As shown, plasma TDP-43 was reduced 30% below baseline at week 12.

FIG. 2 shows plasma TDP-43 percent change versus baseline level. The Y-axis represents the percentage change from baseline, where the mean of percentage change in a group is the mean of the percentage changes in each subject of that group. The X-axis represents individual visits at separate time points, that are not to scale however, such that V4 is 1 week after treatment at the beginning of the second week, V6 is the end of the second week when the sixth and final dosage administration of GM604 was administered, V7 is 6 weeks after baseline, and V8 is 12 weeks after baseline.

FIG. 3 shows plasma total Tau percent change versus baseline level. The Y-axis represents the percentage change from baseline, where the mean of percentage change in a group is the mean of the percentage changes in each subject of that group. The X-axis represents individual visits at separate time points, that are not to scale however, such that V4 is 1 week after treatment at the beginning of the second week, V6 is the end of the second week when the sixth and final dosage administration of GM604 was administered, V7 is 6 weeks after baseline, and V8 is 12 weeks after baseline.

FIG. 4 shows plasma total SOD1 percent change versus baseline level. The Y-axis represents the percentage change from baseline, where the mean of percentage change in a group is the mean of the percentage changes in each subject of that group. The X-axis represents individual visits at separate time points, that are not to scale however, such that V4 is 1 week after treatment at the beginning of the second week, V6 is the end of the second week when the sixth and final dosage administration of GM604 was administered, V7 is 6 weeks after baseline, and V8 is 12 weeks after baseline.

FIG. 6 (C, D) Show simulation analyses. Sets of 156 SH-SY5Y-expressed genes were sampled at random. In (C), the histogram shows the average FC among sets of 156 randomly sampled genes (arrow: observed average FC among 156 ALS-associated genes). In (D), the histogram shows the average value of $2^{abs[log\ 2(FC)]}$ for each randomly sampled gene set, representing the average non-directional change in gene expression (arrow: observed value among 156 ALS-associated genes).

DETAILED DESCRIPTION

Figure 1:
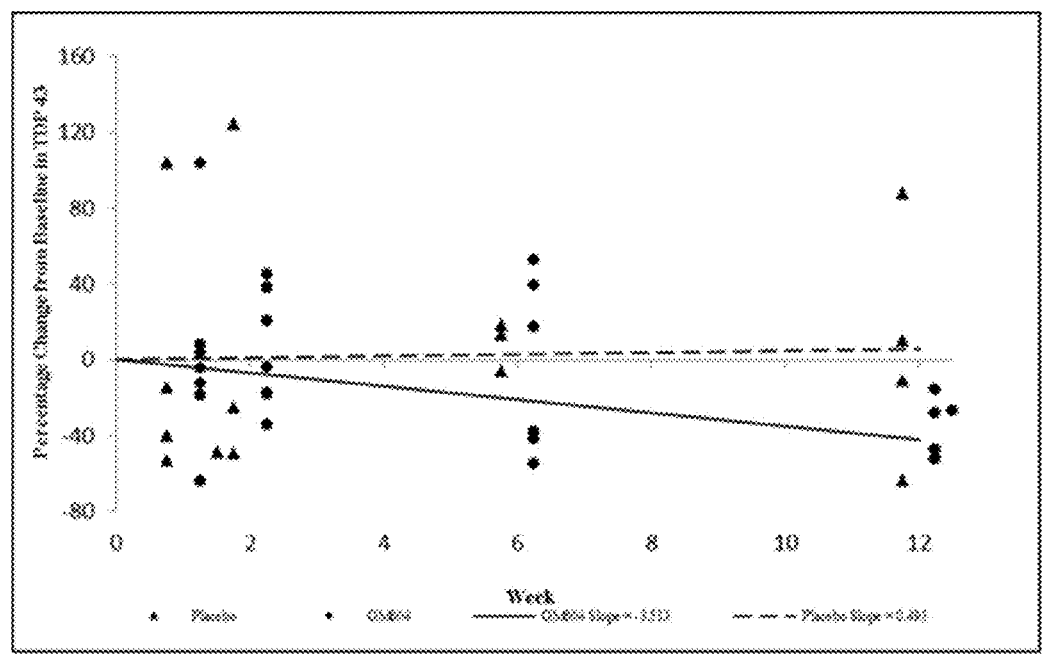
In FIG. 1 to FIG. 4, The Y-axis represents the percentage change from baseline, where the mean of percentage change in a group is the mean of the percentage changes in each subject of that group.

The isolation and characterization of two motoneuronotrophic factors (MNTF1 and MNTF2) from rat muscle tissues, as well as the subsequent cloning of a recombinant MNTF1-F6 gene derived from a human retinoblastoma cDNA library, is previously described in Applicant's prior U.S. Pat. No. 6,309,877. The MNTF1-F6 gene sequence encodes a 33 amino acid sequence referred to herein as SEQ ID NO:1 having the following amino acid sequence:

[SEQ ID NO: 1]
LGTFWGDTLNCWMLSA*FSRYAR*CLAEGHDGPTQ.

The naturally occurring and recombinant MNTF1 polypeptides were shown to selectively enhance the survival in vitro of anterior horn motor neurons isolated from rat lumbar spinal cord explants. Photomicrographs of treated cultures exhibited neurite outgrowth of myelinated nerve fibers and a marked reduction in the growth of non-neuronal cells, e.g. glial cells and fibroblasts. Similarly, in vivo administration of MNTF1 to surgically axotomized rat peripheral nerves resulted in a markedly higher percentage of surviving motor neurons than untreated controls, which could be blocked by co-administration of anti-MNTF1 monoclonal antibody.

Further beneficial effects of MNTF1 were demonstrated in rats subjected to spinal cord hemi-section, repaired by a peripheral nerve autograft and implanted with MNTF1-containing gel sections in close proximity to the nerve graft junctions with spinal cord. MNTF1 treated animals exhibited greater numbers of surviving motor neurons, improved recovery of motor and sensory function, reduced inflammatory response (fewer infiltrating macrophages and lymphocytes) and reduced collagen-containing scar tissue formation at the site of the graft, normal Schwann cell morphology and normal myelinated and non-myelinated nerve fiber formation.

The proposed approach of using neurotrophic growth factors for the treatment of amyotrophic lateral sclerosis has been studied a lot in the 1990s. Recent review bring back interest to the use of neurotrophic growth factors, despite possible reasons for clinical failure in the past and reasons for a renewal of hope in this powerful class of drugs for the treatment of ALS. (Henriques A et al. 2010, Neurotrophic Growth Factors for the Treatment of Amyotrophic Lateral Sclerosis: Where do we stand? Frontiers in Neuroscience. Vol 4. Article 32, 1-14).

Motoneurono Trophic Factor (MNTF) peaks in expression during week 9 in human fetus gestation period. (Di, X. Et al. 1998. Localization and morphometric study on Motoneuronotrophic factor 1 and its receptor in developing chorionic villi of human placenta. Acta Anatomica Sinica 29: 86-89). This expression of MNTF in the developing human embryo prompted us to reason that MNTF may promote the differentiation and/or survival of motor neurons. Indeed, in U.S. Pat. No. 8,986,676, it was shown that MNTF and its peptide analog with retinoic acid have induced differentiation of embryonic stem cell into motor neuron and induced proliferation of the neurons. MNTF or its analog also demonstrated neuroprotective effect via a protein kinase pathway which is modulated by a sonic hedgehog independent pathway to ameliorate or inhibit the progression of neuronal disorder. The inventors have also shown that MNTF is involved in modulating the expression or activity of one or more proteins including a tyrosine kinase, a growth factor, a insulin receptor, IGF-1 receptor, IGF-2 receptor, Shh, Akt, Bad (Bcl-2 antagonist of cell death), PI (3,4,5) P3-dependent kinase (PDK1), Bax, p53 gene product, pp60-Src, JAK 2, nitric oxide synthases (NOS), glycogen synthase kinase 3 (GSK), caspase, PI3 kinase (Phosphatidylinositol 3-kinase), and Ras.

Two previously unrecognized overlapping domains within the MNTF1-F6 molecule that appear to be sufficient for the known biological activities of MNTF1 have now been identified. Each of these domains, designated herein as the "WMLSAFS" (SEQ ID NO: 3) and "FSRYAR" (SEQ ID NO: 2) domains, are sufficient to stimulate the proliferation of motor neuron derived cell lines in a manner similar to the MNTF1-F6 33-mer. Similarly, the "FSRYAR" domain (SEQ ID NO: 2) is sufficient to direct selective reinnervation of muscle targets by motor neurons in vivo in a manner similar to the MNTF1-F6 33-mer. In addition, the "FSRYAR" domain (SEQ ID NO: 2) provides an antigenic epitope sufficient to raise antibody that recognizes any MNTF peptide containing the "FSRYAR" sequence (SEQ ID NO: 2), including the MNTF1-F6 33-mer.

Novel peptides and composition from active fragments of MNTF that are capable of modulating viability and growth in neuronal cells, and to methods of modulating neuronal cell viability and growth employing the novel peptides and compositions, containing either a "WMLSAFS domain" (SEQ ID NO: 3) or "FSRYAR domain" (SEQ ID NO: 2), which is sufficient for neurotrophic or neurotropic function is described in U.S. Pat. No. 7,183,373. The polypeptide domain demonstrated therein were sufficient for the selective maintenance and axonal regeneration of neuronal cells, and to peptides and/or molecules capable of mimicking their structure and/or function. Preferred embodiments of that invention comprise a peptide having the amino acid sequence: FSRYAR [SEQ ID NO:2], the sequence of GM6, also known as GM604 for ALS indication, as well as analogues thereof. Preferably such analogues are functional equivalents of the GM604 [SEQ ID NO:2].

Novel peptides and composition from active fragments of MNTF that are capable of modulating viability and growth in neuronal cells, and to methods of modulating neuronal cell viability and growth employing the novel peptides and compositions, containing either a "WMLSAFS domain" or "FSRYAR domain", which is sufficient for neurotrophic or neurotropic function is described in U.S. Pat. No. 7,183,373. The polypeptide domain demonstrated therein were sufficient for the selective maintenance and axonal regeneration of neuronal cells, and to peptides and/or molecules capable of mimicking their structure and/or function. Preferred embodiments of that invention comprise a peptide having the amino acid sequence: FSRYAR [SEQ ID NO:2], the sequence of GM6, also known as GM604 for ALS indication, as well as analogues thereof. Preferably such analogues are functional equivalents of the GM604 [SEQ ID NO:2].

GM604 is the active domain of MNTF, an endogenous master neural growth regulator present during the fetal development phase when neurons are being created and reaching terminal synaptic targets. The fetal phase is the most intense and rapid period of human growth and development, especially within the CNS. In preclinical studies, treatment of GM604 in rodents demonstrated that it promotes neural regeneration and exhibit both the trophic and tropic effects (Chau R M W et al. 1990 Neurotrophic Factor. Chin 3. Neuroanat. 6:129-138; Chau R M W et al. 1992. Muscle neurotrophic factors specific for anterior horn motoneurons of rat spinal cord. Recent Adv. Cell Mol Biol. 5:89-94; Yu J. et al. 2008. Motoneuronotrophic Factor analog GM604 reduces infarct volume and behavioral deficits following transient ischemia in the mouse. Brain Res. 1238:143-153: U.S. Pat. No. 7,183,373).

From the inventors in vitro and in vivo studies, we now understand that the MNTF 6 mer described herein and referred to as GM604 involves multiple mechanisms of action. GM604 binds to the insulin receptor and causes autophosphorylation of Tyr 1162/1163 of insulin receptor and IGF-1 (U.S. Pat. No. 8,986,676). GM604 also activates and modulates pathways through PI3K, as shown in the in vitro study with SH-SY5Y cells Parkinson Disease model, treatment with wortmannin (PI3K inhibitor) abrogated the effects of MNTF, implying effect through PI3K pathway (U.S. Pat. No. 8,673,852). The inventors have also shown the role of GM604 in anti-apoptosis, neurogenesis and anti-inflammation. In U.S. Pat. No. 8,673,852, the inventors showed that GM604 was able to penetrate the blood brain barrier.

A biomarker is defined as any characteristic that is objectively measured and evaluated as an indicator of normal biological processes, pathogenic processes or pharmacogenomics processes to a therapeutic intervention. Both the FDA and EMA recognize the increasingly important role of biomarkers in the drug-development process. For devastating diseases, a search of disease-related biomarker can expedite the identification of a drug target. The use of disease-related biomarker as surrogate end points in clinical trials has expedited drug approval in oncology. The potential clinical benefits for disease-specific biomarkers include a more rapid and accurate disease diagnosis, and potential reduction in size and duration of clinical drug trials, which would speed up drug development. The application of biomarkers into drug development of ALS disease should both determine if a drug hits its proposed target ("target biomarkers") and whether the drug alters the course of disease ("efficacy biomarkers").

A surrogate end point is defined as a biomarker that is intended to substitute for a known clinical end point, such as in the case of ALS. A surrogate endpoint is expected to predict benefit (or harm, or lack of benefit) based on epidemiologic, therapeutic, pathophysiologic or other scientific evidence. (Biomarkers Definitions Working Group (2001), Biomarkers and surrogate endpoints: preferred definitions and conceptual framework. Clin. Pharmacol. Ther.; 69(3):89-95) Such biomarkers are also frequently used to monitor disease progression in response to therapy.

The diagnosis of ALS is currently limited to evaluations based upon a clinical examination, electrophysiological findings, medical history, and exclusion of confounding disorders. ALS can be difficult to diagnose during the early stages, and the diagnostic process takes as long as between 13 to 18 months. (A. Radunovih et al. 2007. Clinical care of patients with amyotrophic lateral sclerosis, The Lancet Neurology, vol. 6, no. 10, pp. 913-925). Reliable biomarkers can serve as a surrogate of disease progression, which would allow the objective measurement of secondary endpoint for drug efficacy rather than relying solely on survival or the revised ALS functional rating scale (ALSFRS-R). ALSFRS-R is a quality-of-life scale but with low sensitivity. Other commonly used clinical measures include muscle strength testing by grip strength machine or Hand Held Dynamometer), respiratory function testing reported as forced vital capacity (FVC). None of these measurements provides any insight into the biological mechanisms of disease or disease progression. Therefore, many investigators for ALS have searched for biomarkers of ALS for provide disease progression to provide insight into the mechanisms of disease.

Despite intensive research that has been conducted over the past 20 years, we also do not currently have practical diagnostic biomarkers. Currently there are no reliable and robust biomarkers capable of indicating the progression of ALS in the clinic or for therapeutic trials. A reliable progression marker should enable shorter trials on a smaller number of patients to be conducted. (H. Ryberg et al. 2008. Protein biomarkers for amyotrophic lateral sclerosis. Expert Review of Proteomics. vol. 5, no. 2, pp. 249-262; M. R. Turner et al, 2009. Biomarkers in amyotrophic lateral sclerosis. The Lancet Neurology. vol. 8, no. 1, pp. 94-109.). An absence of reliable prognostic biomarkers combined with a lack of understanding of the mechanisms underlying ALS is a substantial problem for furthering the understanding and treatment of this devastating disease. Over the last two decades the search for biomarkers has been relentless, and yet none of the proposed biomarkers has been translated into effective tools in the clinical setting. Two obstacles that have been neglected but which are vital toward achieving a better understanding and potential treatments for ALS are developing reliable prognostic biomarkers and a multi-target approach that is not dependent on one single mechanism. Both of these vital components are provided by the instant invention.

In this subject invention, we have identified a combination of biomarkers that are prognostic of ALS and we have shown that GM604 is capable of regulating these biomarkers. With data collected from a Phase 2A double blinded randomized placebo controlled clinical trial with GM604 in ALS patients, GM604 demonstrated its ability to bring homeostasis in several ALS disease related genes, especially TDP-43, SOD1 and Tau with statistical significance when the plasma biomarkers levels in GM604 treated patients were compared with placebo treated patients. The data from human clinical trial confirmed in vitro data in DNA microarray and PCR arrays in neuronal cells.

Aspects of the invention may also be described as follows:

1. A method of monitoring ALS, the method comprising the steps of: i) administering GM604 to a subject to regulate at least one biomarker in the subject selected from the group consisting of TDP-43, SOD1, and Tau, ii) monitoring the regulation of the at least one biomarker after administration of MNTF, iii) measuring a known parameter associated with ALS disease progression to make an evaluation of ALS disease progression, and iv) making a determination if the regulation of said biomarker correlates with an ALS disease progression determination.

2. A method of monitoring ALS, the method comprising the steps of: i) administering GM604 to a subject to regulate the a biomarker, wherein the biomarker comprises TDP-43, ii) monitoring the regulation of TDP-43 after administration of MNTF, iii) measuring a known parameter associated with ALS disease progression to make an evaluation of ALS disease progression, and iv) making a determination if the regulation of said biomarker correlates with an ALS disease progression determination.

3. A method of monitoring ALS, the method comprising the steps of: i) administering GM604 to a subject to regulate the a biomarker, wherein the biomarker comprises SOD1, ii) monitoring the regulation of SOD1 after administration of MNTF, iii) measuring a known parameter associated with ALS disease progression to make an evaluation of ALS disease progression, and iv) making a determination if the regulation of said biomarker correlates with an ALS disease progression determination.

4. A method of monitoring ALS, the method comprising the steps of: i) administering GM604 to a subject to regulate the a biomarker, wherein the biomarker comprises Tau, ii) monitoring the regulation of Tau after administration of MNTF, iii) measuring a known parameter associated with ALS disease progression to make an evaluation of ALS disease progression, and iv) making a determination if the regulation of said biomarker correlates with an ALS disease progression determination.

5. A method for monitoring and determining the efficacy of treatment for ALS, the method comprising the steps of: i) selecting a patient, ii) quantifying a biomarker for ALS in said patient, wherein the biomarker is selected from the group consisting of TDP-43, SOD1, and Tau, iii) classifying the patient as in need of treatment for ALS if the quantity of said biomarker is determined to be above a predetermined level for a selected subject, iv) administering GM604 to a subject classified as in need of treatment to regulate the biomarker, and v) correlating the regulation of the biomarker with an improvement in ALS disease progression.

6. A method for monitoring and determining the efficacy of treatment for ALS, the method comprising the steps of: i) selecting a patient, ii) quantifying a biomarker for ALS in said patient, wherein the biomarker comprises TDP-43, iii) classifying the patient as in need of treatment for ALS if the quantity of said biomarker is determined to be above a predetermined level for a selected subject, iv) administering GM604 to a subject classified as in need of treatment to regulate TDP-43, and v) correlating the regulation of the biomarker with an improvement in ALS disease progression.

7. A method for monitoring and determining the efficacy of treatment for ALS, the method comprising the steps of: i) selecting a patient, ii) quantifying a biomarker for ALS in said patient, wherein the biomarker comprises SOD1, iii) classifying the patient as in need of treatment for ALS if the quantity of said biomarker is determined to be above a predetermined level for a selected subject, iv) administering GM604 to a subject classified as in need of treatment to regulate SOD1, and v) correlating the regulation of the biomarker with an improvement in ALS disease progression.

8. A method for monitoring and determining the efficacy of treatment for ALS, the method comprising the steps of: i) selecting a patient, ii) quantifying a biomarker for ALS in said patient, wherein the biomarker comprises Tau, iii) classifying the patient as in need of treatment for ALS if the quantity of said biomarker is determined to be above a predetermined level for a selected subject, iv) administering GM604 to a subject classified as in need of treatment to regulate Tau, and v) correlating the regulation of the biomarker with an improvement in ALS disease progression.

9. A method of prognosis for ALS, the method comprising the steps of: i) administering GM604 to a subject to regulate at least one biomarker in the subject selected from the group consisting of TDP-43, SOD1, and Tau, ii) monitoring the regulation of the at least one biomarker after administration of GM604, iii) measuring a known parameter associated with ALS disease progression to make an evaluation of ALS disease progression, and iv) making a determination if the regulation of said biomarker predicts the ALS disease progression determination.

10. A method of regulating biomarkers in a subject, the method comprising the steps of: i) selecting a subject for administration of GM604, ii) administering the GM604 in an preselected amount to the subject, iii) wherein the administration regulates at least one biomarkers selected from TDP-43, SOD1, and Tau.

11. A method of regulating biomarkers in a subject, the method comprising the steps of: i) selecting a subject for administration of GM604, ii) administering the GM604 in an preselected amount to the subject, iii) wherein the administration regulates the biomarker TDP-43.

12. A method of regulating biomarkers in a subject, the method comprising the steps of: i) selecting a subject for administration of GM604, ii) administering the GM604 in an preselected amount to the subject, iii) wherein the administration regulates the biomarker SOD1.

13. A method of regulating biomarkers in a subject, the method comprising the steps of: i) selecting a subject for administration of GM604, ii) administering the GM604 in an preselected amount to the subject, iii) wherein the administration regulates the biomarker Tau.

14. A method of treating ALS, the method comprising the steps of: i) administering GM604 to a subject to regulate at least one biomarker in the subject selected from the group consisting of TDP-43, SOD1, and Tau, ii) observing the regulation of the at least one biomarker after administration of MNTF, iii) correlating the regulation of the biomarker with an improvement in ALS disease progression.

15. A method of treating ALS, the method comprising the steps of: i) administering GM604 to a subject to regulate a biomarker comprising TDP-43, ii) observing the regulation of TDP-43 after administration of MNTF, iii) correlating the regulation of TDP-43 with an improvement in ALS disease progression.

16. A method of treating ALS, the method comprising the steps of: i) administering GM604 to a subject to regulate a biomarker comprising SOD1, ii) observing the regulation of SOD1 after administration of MNTF, iii) correlating the regulation of SOD1 with an improvement in ALS disease progression.

17. A method of treating ALS, the method comprising the steps of: i) administering GM604 to a subject to regulate a biomarker comprising Tau, ii) observing the regulation of Tau after administration of MNTF, iii) correlating the regulation of Tau with an improvement in ALS disease progression.

18. A method of monitoring ALS, the method comprising the steps of: i) administering GM604 to a subject to regulate at least one biomarker in the subject selected from the group consisting of TDP-43, SOD1, Tau, Cystatin-C, IRS1, IRS2, AKT1, PIK3, and C9orf72, ii) monitoring the regulation of the at least one biomarker after administration of MNTF, iii) measuring a known parameter associated with ALS disease progression to make an evaluation of ALS disease progression, and iv) making a determination if the regulation of said biomarker correlates with an ALS disease progression determination.

19. A method according to any one of claims 1-17, where the administration of GM604 regulates at least one of the following Cystatin-C, IRS1, IRS2, AKT1, PIK3, and C9orf72.

20. A method according to any one of claims 1-18, wherein two or more of the biomarkers are regulated.

21. A method according to any one of claims 1-18, wherein said regulation results in a homeostasis of one or more biomarker.

22. A method according to any one of claims 1-18, wherein said regulation results in a down regulation of one or more biomarker.

23. A method according to claim 22, wherein said down regulation results in a down regulation of the mRNA expression levels one or more biomarker.

24. A method according to claim 22, wherein said down regulation results in a down regulation of the protein expression levels one or more biomarker.

25. A method according to claim 22, wherein said down regulation results in a down regulation of the activity of one or more biomarker.
26. A method according to any one of claims 1-18, wherein said regulation results in an up regulation of one or more biomarker.
27. A method according to claim 26, wherein said up regulation results in an up regulation of the mRNA expression levels one or more biomarker.
28. A method according to claim 22, wherein said up regulation results in an up regulation of the protein expression levels one or more biomarker.
29. A method according to claim 22, wherein said up regulation results in an up regulation of the activity of one or more biomarker.
30. A method according to any one of claims 1, 2, 5, 9, 10, 11, 14, or 15 wherein TDP-43 mRNA amount or expression level was reduced by about 10%, 20%, or about 30% below baseline levels.
31. A method according to any one of claims 1, 2, 5, 9, 10, 11, 14, or 15 wherein plasma TDP-43 protein amount was reduced by about 10%, 20%, or about 30% below baseline levels.
32. A method according to any one of claims 1, 2, 5, 9, 10, 11, 14, or 15 wherein plasma TDP-43 protein amount was reduced by about 30% below baseline levels at week 12.

The following Examples are offered by way of illustration and not by way of limitation.

Example 1

Selection of TDP-43, Tau and SOD1 as ALS Biomarkers

TDP-43 is a pathologic hallmark of ALS and prior studies have shown increased levels of TDP-43 in ALS biofluid samples. (Kasai, T et al. 2009. Increase TDP-43 protein in cerebrospinal fluid of patients with amyotrophic lateral sclerosis. Acta Neuropathol 117:55-62; Noto Y et al. 2011. Elevated CSF TDP-43 levels in amyotrophic lateral sclerosis: specificity, sensitivity, and a possible prognostic value. Amyotrophic Lateral Scler. 12(2): p. 140-143; Steinacker. P. et al. 2008. TDP-43 in cerebrospinal fluid of patients with frontotemporal lobar degeneration and amyotrophic laberal sclerosis. Arch Neurol., 64(11): p. 1481-1487.) A primary feature of ALS is an accumulation of the protein TDP-43, too much of which is toxic to cells. Over 90% of ALS cases exhibit TDP-43 based pathology, developing a treatment that keeps protein levels just right is imperative. Scientists are looking to develop a drug that can target a protective mechanism nonsense-mediated mRNA decay (NMD) triggered by overexpression of wild type (WT) TDP-43. (Barmada S et al. 2015. Amelioration of toxicity in neuronal models of amyotrophic lateral sclerosis by hUPF1. PNAS 112 (25) 7821-7826.) An in vitro study using patient derived motor neurons generated from induced Pluripotent Stem cells (iPS cells) to screen for drugs that reduce expression levels of TDP-43 showed higher levels of TDP-43 can be neurotoxic and generate cytoplasmic aggregates that impede cellular functions. Compounds that reduce TDP-43 level improve the neurite health. (Egawa N et al. 2012. Drug screening for ALS using patient-specific induced pluripotent stem cells. Sci Transl Med 4. 145ra104). GM604 targeted over expression of TDP-43 and lowered TDP-43 levels. The slope in plasma TDP-43 through week 12 in GM604 treated patients (−3.513 pg/mL/wk) is lower than that in placebo treated patients (0.493 pg/mL/wk) with statistical significance, p=0.0078. In this trial TDP-43 plasma was reduced significantly by 30% at week 12 below baseline.

Tau has been a biomarker for neurodegeneration for many years and is extensively marked for Alzheimer's disease. Tau was used as a biomarker to monitor effects of memantine treatment in ALS patients in a phase 2 clinical trial. That trial showed that reduction of Tau levels in ALS patients due to drug treatment correlated to reductions of clinical parameters of ALS disease progression. (Levine T D et al. 2010. A pilot trial of memantine and riluzole in ALS: correlation to CSF biomarkers. Amyotrophic Lateral Sclerosis. 11:514-519). In our ALS Phase 2A trial, plasma Total TAU (evidence of broken axon and continue neuronal degeneration) reduction achieved statistical significance in percentage change between the treated and placebo patients at 6 weeks, p=0.0369.

The toxicity of SOD1 is the result of a gain of toxic function rather than a loss of enzymatic function; thus reducing concentration of the mutant protein is predicted to slow progression of SOD1-linked amyotrophic lateral sclerosis. (Rothstein J D. 2009. Current hypotheses for the underlying biology of amyotrophic lateral sclerosis. Ann Neurol. 65 Suppl 1:S3-9). SOD1 levels tested in animal models by anti-sense oligonucleotide treatment showed SOD1 is a good pharmacodynamics marker and lowering SOD1 prolonged survival. There is a lack of correlation between CSF SOD1 levels and ALS disease severity and progression, suggesting that once patients become sick, SOD1 remains stable throughout the disease course unless there is a treatment that can lower SOD1 level. (Winer L et al. 2013. SOD1 in cerebral spinal fluid as a pharmacodynamics marker for antisense oligonucleotide therapy. JAMA Neurol., 70(2): 201-207). Lowering SOD1 was hypothesized to be a therapeutic strategy and phase 1 clinical trial with intrathecal anti-sense oligonucleotide administration was performed and biofluid SOD1 level was monitored. (Miller T M et al. 2013. An antisense oligonucleotide against SOD1 delivered intrathecally for patient with SOD1 familial amyotrophic lateral sclerosis: a phase 1, randomized, first-in-man study. Lancet Neurol. 12:435-442). The Over expression of wild-type human SOD1 can also be neurotoxic and may more generally be involved in the pathogenesis of ALS. (Graffmo K et al. 2012. Expression of wild-type human superoxide dismutase-1 in mice causes amyotrophic lateral sclerosis. Human Molecular Genetics. 1-10). All these studies suggested that lowering SOD1 may be a therapeutic strategy to treat ALS. In this trial SOD1 plasma in GM604 treated group showed significant reduction trend when compared with placebo group at 2 weeks, p=0.0550.

Biomarker Data Analysis in Phase 2A Clinical Trial

Genervon Biopharmaceuticals engaged Iron Horse Diagnostic. Inc. and its director Robert Bowser, PhD to test and analyze the CSF and Plasma biomarkers data from GALS-001 Phase 2A clinical trial. The same biomarker assays are used to test CSF and plasma biomarkers. The plasma biomarkers show more robust results than CSF biomarkers. Biomarker data is basically not able to be influenced by placebo effect. The biomarker study was designed to illuminate whether GM604 might modulate certain genes (e.g. target biomarkers), a process that may take hours to change the protein expression and days or weeks to improve the neurological system.

In the trial summarized in Table 1, five biomarkers were tested and data collected. As shown in the Table GM604 modulated one target (SOD1 Plasma and CSF), one efficacy (Total TAU Plasma), two target/efficacy biomarkers (TDP-43 Plasma and Cystatin C CSF) and one prognostic biomarker (pNFH CSF).

TABLE 1

| Grouping | Biomarkers | GM604 Treated Arm | Placebo Arm | PCR data (SH-SY5Y) | Comments |
|---|---|---|---|---|---|
| A. Target Biomarkers | 1. SOD1 Plasma | ↓ Reduced Significantly p = 0.055 @2 weeks | ↑ Increase | ↓2 fold @ 4 hr | Significant Reduction, SOD 1 is a target of GM604 |
| | SOD1 CSF | ↓ Reduced Significantly @wk 6 | ↑ Increase @ week 6 | | SOD 1 is a target of GM604 |
| B. Efficacy Biomarkers | 2. Total Tau Plasma | ↓ Reduced Significantly 28% below BL p = 0.0369 @ 6 weeks | ↑ Opposite pattern of Treated | N/A | Statistically Significant Reduction |
| C. Target/ Efficacy Biomarkers | 3. TDP-43 Plasma | ↓ Reduced Significantly 30% below BL p = 0.0078 slope @12 weeks | ↑ Increase | ↓2-3 fold @12 hr thru 48 hr | Neuroprotective. GM604 targeted TDP-43 and lowered TDP-43 levels. Statistically Significant Reduction |
| | 4. Cystatin C CSF | ↑ Increase @week 6 | ↓ Decrease @week 6 | ↑2fold@ 12 hr | Neuroprotective |
| D. Prognostic Biomarkers | 5. pNFH CSF | ↓ Decrease | ↓ Less Decrease | N/A | ALS patients pNFH are >400 pg/ml in CSF and >50 pg/ml in plasma. Higher pNFH higher disease Progression Rate |

The observed effects of GM604 on TDP-43, SOD1 and Cystatin C are consistent with the Neuroprotective properties of GM604 reported in previous Genervon's PCR studies of GM604 with SH-SY5Y cells as presented in Example 2.

Biomarkers data may have confirmed the hypotheses and show a trend that GM604 (1) is a master regulator that cure ALS diseases by responding to distress signals from multiple affected genes (targets), (2) modulates multiple genes by up and down regulate each gene closer to a normal range, and (3) brings homeostasis of affected biological systems.

Single target drug molecules such as antibody, inhibitor or blockers usually are uni-directional, e.g. stopping the effect of certain undesirable gene expressions or increase certain gene expression to compensate for the lack thereof. Master regulator peptide drug is not only modulating multiple targets but in each gene the master regulator modulation should be bi-directional depending on the distress signals from the targeted gene. This behavior is consistent with our DNA micro-array and PCR array studies results.

Results of the Disease Progression Analyses for the CSF Biomarkers

There were no statistically significant differences in the slopes between GM604 and placebo for the CSF biomarkers, although there was one non-significant sizable difference at week 6 as shown on Table 1. The slope for GM604 for SOD1 was −1.874 through Week 6 and 15.225 for placebo. The baseline SOD1 level in the CSF of GM604 treated patient 0201 was four fold that of other ALS patients in this trial. His SOD1 CSF level was reduced by 50% at end of drug treatment and remained 40% below basal level at the end of study. His ALSFRS-R rate of progression was reduced when compared to historic controls.

Cystatin C is often reduced in the CSF of ALS patients versus controls. Increasing CSF Cystatin C could have a neuroprotective effect. In the clinical trial biomarker testing CSF Cystatin C level had modest increase in treated group (slope=0.786 @ week 6) but decrease in placebo group (slope=−2.284 @ week 6), although no statistical significance. The clinical biomarker test results seem to confirm that Cystatin C is both a target and efficacy marker of GM604.

ALS patients pNFH are >400 pg/ml in CSF and >50 pg/ml in plasma. The higher the pNFH, the higher disease Progression Rate. GM604 treated group had decrease in the CSF pNPH levels while the placebo had less decrease, although no statistical significance.

Results from Three Plasma Biomarkers: TDP-43, Total Tau and SOD1

FIG. 1 is a plot showing percentage change in plasma TDP 43 from baseline vs. Time through Week 12. Shown on the X-axis are time points in weeks, including at 0, 2, 4, 6, 8, 10, 12 weeks. Plasma TDP-43 was reduced 30% below baseline at week 12. The slope from baseline to week 12 were −3.513 and 0.493 for GM604 treated group and placebo group respectively, p=0.0078.

Significant differences in percentage change between the GM604 treated and placebo patients were also observed in Plasma Total Tau at 6 weeks (p=0.0369) and SOD1plasma at 2 weeks (p=0.055).

Figure 2:
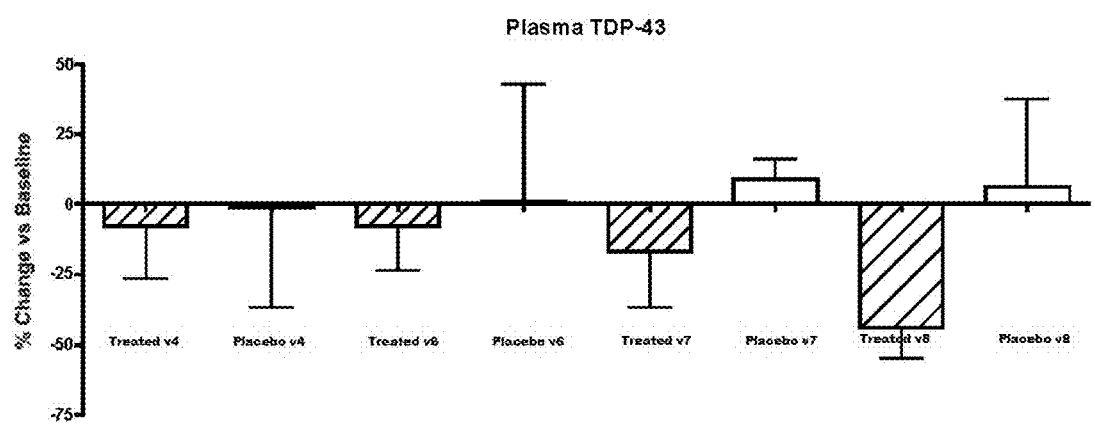

FIG. 2 is a bar chart showing plasma TDP-43 percent change versus baseline level. The X-axis represents individual visits at separate time points. TDP-43 is a gene modulated (decreased transcription) by GM604 and thus is also a target of the drug. When TDP-43 data is graphed as percent change over time versus baseline, the GM604 treated group exhibited decreases at each visit when compared to baseline, with more significant decreases by visit 8. Subject 0101 is removed from this analysis due to hemolysis of the baseline plasma sample. The placebo group displayed small decreases at visit 4, and modest increases at visits 7 and 8. The slope in plasma TDP-43 through week 12 in GM604 treated (−3.513 pg/mL/wk) is lower than placebo (0.493 pg/mL/wk) with statistical significance, p=0.0078. It appears that GM604 may have targeted TDPDP TDPDPhat GM604 may have targeted TDPDP TDPDP signify a good indication for modulating neurodegeneration.

Figure 3:
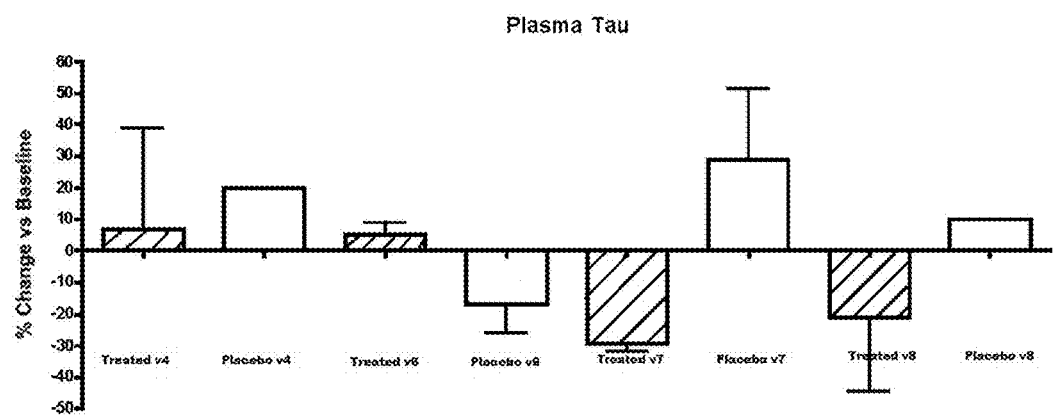
Figure 4:
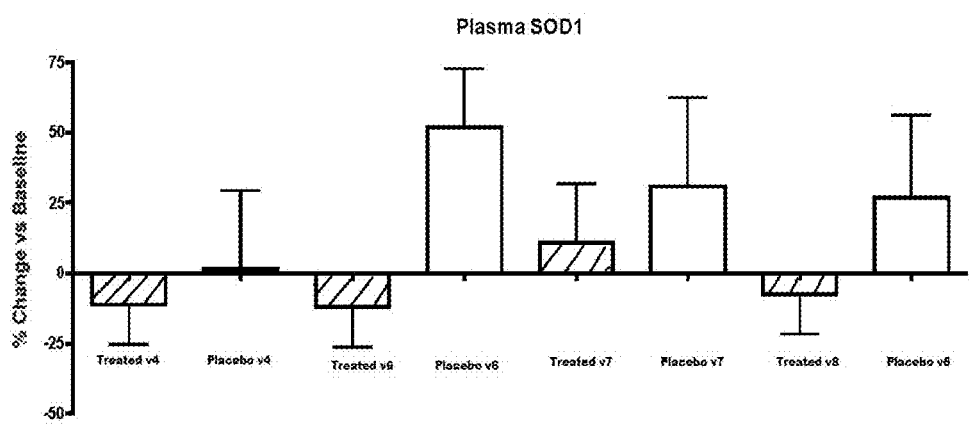
Figure 5:
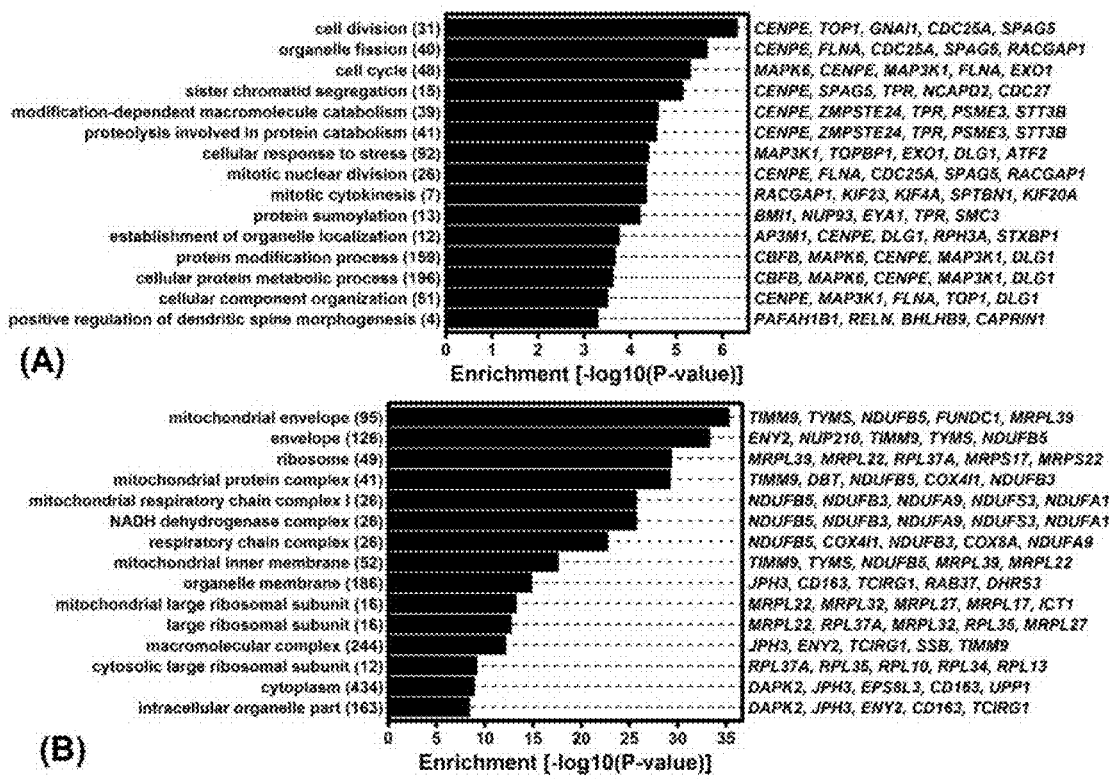
FIG. 5. Shows a gene ontology (GO) analyses for GM6 regulated genes. 5 (A) shows biological process (BP) terms enriched among 581 genes strongly up-regulated by GM6 (FDR<0.10; FC>2.0). 5 (B) shows Cell component (CC) terms enriched among 678 genes strongly down-regulated by GM6 (FDR<0.10; PC<0.50). In (A) and (B), p-values for each GO term were generated from a conditional hypergeometric test evaluating whether GM6-increased/decreased genes were more frequently associated with the term as compared to all other expressed genes. Parentheses (left margin) indicate the number of GM6-increased/decreased genes associated with the listed term. Genes most strongly increased/decreased by GM6 and associated with each term are shown in the right margin.

For Plasma total Tau, when the results are graphed as a percent change over time versus baseline (FIG. 3) at individual visits at separate time pointes, we noted reductions in plasma total Tau at visits 7 and 8 for the GM604 group, but no consistency was observed in the trend of the placebo group. At visit 7 (6 weeks) the GM604 treatment group exhibited a reduction in plasma total Tau and the placebo group an increase in plasma total Tau that is statistically significant (p=0.0369). Subject 0202 (1,527 pg/ml-outlier) is removed from the placebo group in this figure The SOD1 gene is modulated (decreased transcription) by GM604 (prior Genervon in vitro data results) and therefore is a target of the drug. As shown in FIG. 4, the percent change of SOD1 levels in plasma over time verses baseline at individual visits at separate time points, exhibited a trend with near statistically significant reduced levels in the GM604 treated patients versus the placebo group at the end of the treatment time (v6, p=0.055). Also, GM604 treated patient 0101 exhibited a sharp reduction in SOD1 levels in the plasma between visits 4 and 6 during drug treatment (drop of 60% from 360.52 ng/ml to 143.93 ng/ml), suggesting a drug effect. This drop in SOD1 levels suggests that GM604 may modulate gene expression towards a more homeostatic level typical of healthy adults. The baseline plasma sample for patient 0101 was hemolyzed and therefore this subject was not included in the data analysis of percent change versus the baseline. The trends observed in this study would suggest that GM604 may be modulating abnormal SOD1 protein levels in the CSP and blood of ALS patients.

GM604 Regulates Homeostasis

In addition to testing the biomarker changes in Phase 2A trial patient population, biomarkers changes were also tested and analyzed with samples from the single, very advanced ALS patient who was treated with GM604 with the approval of the FDA through compassionate use. He has biomarker have those biomarker data above the normal range and they were lowered by GM604. This advance patient whose biomarker levels were below normal had the same biomarker levels increased. This is the hallmark of homeostatic process for the health of living organism.

Example 2

Biomarker Data and Pre-Clinical mRNA PCR Array Data

Another aspect of the invention is the regulation of various targets of GM604 at the mRNA level, as well as the quantification and correlation of this regulation of GM604 targets by in vitro techniques such as the use of microarrays and PCR. Prior to the GALS-001 clinical trial, Genervon explored what genes are modulated by GM604 by in vitro methods in DNA microarray and PCR array. The DNA microarray quantified the effect of GM604 on the gene expression profile in the SH-SY5Y (neuroblastoma) cells, using DNA microarray technique. The resulting data were then analyzed with Genesifter software.

A study with PCR array was carried out with a number of ALS genes that were modulated in DNA microarray. SH-SY5Y cells were incubated in the presence and absence of GM604. GM604 was co-cultured with SH-SY5Y cells at multiple concentrations.

RNAs were extracted at 2 hours, 4 hours, 12 hours, 24 hours and 48 hours from the culture incubated with GM604, and compared with RNA extracted at 0 hour and 48 hour from the control samples. The extracted RNAs were purified and assessed the fold regulation in comparison with control sample at 0 hour. The expression of genes of interest was measured by real-time quantitative PCR with PCR with BioRad Detection System.

In the PCR array study, there is a dose dependent effect on modulation by GM604. The modulation effect was also observed longitudinally at 0, 2, 4, 12, 24, 48, hours, with control observed at 0 hr and control at 48 hr. PCR array confirmed that GM604 modulates the mRNA levels corresponding to the same way GM604 modulates the genes in the DNA microarray.

The results of Fold changes of purified total RNA in real-time quantitative PCR of SH-SY5Y cells incubated with GM604 and extracted RNA at various time points are summarized below.

TABLE 2

| | Gene | | | | | | |
| --- | --- | --- | --- | --- | --- | --- | --- |
| | Control | GM604 | GM604 | GM604 Time | GM604 | GM604 | Control |
| | 0 HR | 2 HR | 4 HR | 12 HR | 24 HR | 48 HR | 48 HR |
| SOD1 | 1 | 0.53 | 0.48 | 0.76 | 0.83 | 0.94 | 1.02 |
| TARDBP | 1 | 0.83 | 0.62 | 0.39 | 0.52 | 0.48 | 1.02 |
| IRS2 | 1 | 1.53 | 1.76 | 1.92 | 1.75 | 1.39 | 0.97 |
| AKT1 | 1 | 1.23 | 1.57 | 1.93 | 1.75 | 1.36 | 1.09 |
| CST3 | 1 | 1.53 | 1.84 | 2.11 | 1.59 | 1.35 | 1.05 |
| IRS1 | 1 | 1.63 | 1.95 | 2.34 | 2.11 | 1.54 | 1.11 |
| PIK3C2A | 1 | 1.73 | 1.54 | 1.69 | 1.42 | 1.05 | 1.05 |
| C9orf72 | 1 | 0.53 | 0.69 | 0.48 | 0.72 | 0.83 | 1.01 | values below the normal range at baseline before treatment as we have predicted. GM604 increased the expression of SOD1, Tau and Cystatin C from the baseline data. The importance of this data is that it showed that GM604 can modulate the same biomarkers in both directions. Most ALS patients in the Phase 2A trial within 2-years of disease onset There are a large number of genes related to ALS disease that were modulated in both DNA microarray and PCR array of GM604, indicating that these genes may be targeted by GM604. However the biomarkers for ALS are at an early stage of development and very few good assays were developed and none of them is validated. Therefore Genervon selected only SOD1, TDP-43 (TARDBP) and Cystatin C (CST3) from the PCR array tested list and tested for protein expressions in the GALS-001 clinical trial patient CSF and plasma samples and found correlations between the PCR array results and the clinical trial biomarker test results.

One of the therapeutic strategies to treat ALS is by lowering SOD1. For SOD1, in the clinical trial biomarker test results, SOD1 levels in both CSF and plasma are reduced at the end of drug treatment (when samples are collected 2-6 hours after dosing at visit 6), but does not continue to go down and gradually return to a level between baseline and end of drug treatment. As seen in the PCR array, the effect of GM604 at 4 hours lowers SOD1 level to 0.48, but does not lower the expression of SOD1 at 48 hours anymore. This may explain why the effects of GM604 on SOD1 levels are more prominent and imminent at the end of drug treatment but not as prominent after cessation of drug treatment. The biomarker results seem to confirm SOD1 is a target of GM604.

The effect of GM604 on TDP-43 (TARDBP) seems to be longer lasting as shown on the PCR array results. At 48 hours, TDP-43 level still remained low at 0.48. We did not test beyond 48 hours to see how long the effect will last. This may explain why GM604 treatment has a significant effect on the plasma biomarker TDP-43 across the time interval of 12 weeks, with p=0.0078 when comparing slope from baseline to week 12 between GM604 treated and placebo. The biomarker test results seem to confirm that TDP-43 is a target of GM604.

Cystatin C is often reduced in the CSF of ALS patients versus controls. Increasing CSF Cystatin C could have a neuroprotective effect. Cystatin C (CST3) was tested in PCR array and showed fast increase at 2 hours, peaked at 12 hours, then the modulation effect gradually decreases but still has some effect at 48 hours. GM604 effect on Cystatin C may be longer lasting than SOD1 but not as long lasting as in TDP-43. That may explain why in the clinical trial biomarker testing that CSF Cystatin C level had modest increase in treated group. The clinical biomarker test results seem to confirm that Cystatin C is both a target and efficacy marker of GM604.

Example 3

HUMAN DATA: Biomarker and Clinical Evaluation of GM604 for Detection and Prognosis of ALS A trial with the title "GM604 Phase 2A randomized double-blind placebo controlled Pilot Trial in Amyotrophic Lateral Sclerosis Disease (ALS)" was completed in 2014. (Protocol no. GALS-001, IND #118420; clinicaltrials.gov NCT01854294) The Phase 2A trial was designed to test for safety and to determine whether a six-dose treatment will initiate the disease modification process in ALS patients, such modification to be observed by clinical outcome and measured by biological effects as evidenced by biomarker changes. Both biomarker and clinical data in this small trial demonstrated positive effect in disease modification. Molecular (biomarker) measures in particular are usually immune to change as a result of the psychology of the patient commonly known as placebo effect. The biomarkers data showed that most treated patients are good responders to GM604 treatment in ALS disease modification.

A total of twelve patients were enrolled in the ALS Phase 2A study. Six subjects enrolled at Site 1 and six subjects enrolled at Site 2. Dosing was by slow bolus intravenous administration, once a day for 3 times a week for 2 weeks. Eight patients were randomized to receive 320 mg GM604 per dose and four patients to receive placebo. Our inclusion/exclusion criteria required the ALS patients in the Phase 2A trial to be "definite" ALS sufferers according to El Escorial criteria (i.e., the disease progression must involve upper and lower motoneuron and the bulbar region) who had experienced disease onset within 24 months prior to the beginning of the trial. The goal is to enroll fast progressing patients. Our dosing regimen was delivered via intravenous bolus dosing three times a week (Monday, Wednesday, Friday) for two consecutive weeks, for a total of 6 doses. There was no dosing after the two weeks' treatment, and the patients were followed and evaluated for the next ten weeks. The clinical data for the ALSFRS-R, FVC, TUG, and the Grip Strength and HHD were measured at Baseline, Week 2, Week 6, and Week 12.

The primary endpoint was the percentage change at week 12 from baseline of each biomarker in the CSF of each subject. Secondary endpoints include percentage change of CSF or plasma biomarkers from baseline to different time points, progressive change in clinical outcomes from baseline to different time points for ALSFRS-R, FVC, grip strength, muscle strength and Time Up and Go test (TUG). Secondary analyses also include comparison of slopes (change in the rate of decline) for any hint of disease modification. Additionally, placebo patients from a large database of recent clinical trials by the Northesat ALS Consortium (NEALS) were matched for baseline features and showing stable rates of decline as historical controls. The biomarker data and the clinical data are presented in the following pages.

GALS001 trial data showed that GM604 can start the healing process of ALS by six doses treatment and showed how long the healing process can sustain. Our clinical data showed that the most robust drug effect is at visit 6 (right after the last dosing at Week 2) and visit 7 at Week 6 (4 weeks after end of dosing) but less robust by visit 8 at Week 12 (10 weeks after dosing).

Because this Phase 2A trial is a pilot study with a very small sample size, it is not reasonable to expect useful levels of statistical power. The goal was to confirm safety and to find significant efficacy trends in not only clinical data but to correlate with biomarkers data. An unexpected surprise is that both clinical and biomarker data in this small trial have big treatment effect and are well correlated.

Summary of Clinical Data

The clinical endpoints for the ALSFRS-R, FVC, TUG, and the Grip Strength and HHD were measured at Baseline, Week 2, Week 6, and Week 12. This summary will focus on the FVC and ALSFRS. The Grip Strength and HHD assessments had great variability due to the different handedness of the patients along with the disease potentially affecting one side of the body in a slightly different manner than the other side. The Grip Strength and HHD results will not be presented here. TUG is also not a good clinical measurement for ALS trial because as ALS disease progressed, many ALS patients will not be able to perform TUG, such as in this trial, 50% of placebo patient were not able to perform TUG at week 12. TUG results will not be reported in here.

FVC

The Forced Vital Capacity (FVC) measures the maximal volume of gas that can be expired as forcefully and rapidly as possible after a maximal inspiration to total lung capacity. This measurement will help determine the patient's breathing ability. The operator of the spirometry machine will reset the machine, start and stop the FVC data collection. The testing procedure requires a lot of coaching from the evaluator: instruct the patient to have an abrupt and unhesitating start, smooth and continuous exhalation until complete, no coughing during first second, instruct the patient to inspire fully as rapidly as possible, instruct the patient to exhale as rapidly, forcefully, and completely as possible (a minimum of six-seconds of exhalation is recommended), minimum of three acceptable efforts, repeatable, acceptable efforts to breathe normally through the pneumotach. Because the accuracy of FVC measurement depends a lot on the operator/evaluator's coaching, the same operator/evaluator should perform FVC testing on the same patient at different time points to avoid inter-rater error.

At Site 1, same operator/evaluator performed all the FVC measurements. At Site 2, several different operators/evaluators performed PVC measurements even for the same patient and is more probable to have inter-rater variability. Also, out of only 8 patients enrolled, one of the patient enrolled at Site 2 was from a foreign country and did not come back for visit 12 PVC data collection and only left with PVC data from 7 patients. That renders the Site 2 FVC data not as reliable as Site 1 data. In the pre-specified analysis of FVC from baseline to visit 12 for both Site 1 and Site 2 combined, there were trends for improvements, (Table 3, −11.5 vs −4.7). In light of Site 2 FVC data not being reliable, FVC data from Site 1 alone is analyzed. Statistically significant differences were observed in change from baseline to week 12 when comparing treatment with placebo using data from Site 1 (Table 4, −28 vs 4.8, p=0.0268). Statistical analysis of the FVC data are presented in the following tables:

TABLE 3

Change from Baseline to Week 12 in FVC

| Time Point | Placebo | GM604 |
| --- | --- | --- |
| Baseline | | |
| N | 4 | 7 |
| Mean | 81.3 | 91.1 |
| Week 12 | | |
| N | 4 | 7 |
| Mean | 69.8 | 86.4 |
| Change from Baseline | | |
| N | 4 | 7 |
| Mean | −11.5 | −4.7 |

TABLE 4

Change from Baseline to Week 12 in FVC at Site 001

| Time Point | Placebo | GM604 |
| --- | --- | --- |
| Baseline | | |
| N | 2 | 4 |
| Mean | 73.5 | 89.5 |
| Week 12 | | |
| N | 2 | 4 |
| Mean | 45.5 | 84.8 |
| Change from Baseline | | |
| N | 2 | 4 |
| Mean | −28.0 | −4.8 |
| P-values | | |
| Two-sample t Test | | 0.0268 |
| Wilcoxon Rank Sum Test | | 0.1052 |

The fact that these p-values are significant at one site, or approaching significance with the nonparametric Wilcoxon Rank Sum Test, with so few patients is remarkable. The six doses over two weeks seemed to have started the disease modification process.

ALSFRS-R

ALSFRS-R is a disease specific subjective functional rating scale for the ALS patient to answer 12 questions, with 4 being fully functional and 0 being totally not functional. It is assumed that a healthy person has ALSFRS-R score of 48. As ALS disease progresses, the score decreases. ALSFRS-R is a commonly used clinical outcome endpoint, but it is susceptible to the placebo effect and lowers the power of the study. All the ALS patients enrolled in Phase 2A trial are diagnosed as definite per El Escorial criteria and their disease progression as faster than average. Their ALSFRS-R should decrease faster than average ALS patient. Even though there were no significant differences between GM604 and placebo in the decline of ALSFRS-R score at week 12, the smaller decrease in ALSFRS-R showed a trend of disease modification when compare GM604 treated with placebo patients, −2.7 vs −3.5 respectively (−4.7% versus −9% respectively) in ALSFRS-R score.

In a comparison between the slope of ALSFRS-R decline before and after treatment, the slope for the placebo group changes minimally before (−0.037/day) and after (−0.034/day) treatment, while the slope for the GM604 group changes noticeably before and after treatment from −0.046/day before treatment to −0.032/day after treatment. It was found that the slope for the active treatment changed had a 30% decrease in slope compared to before the treatment. GM604 in Phase 2A ALS trial achieved a positive trend of slowing down disease progression as measured by ALSFRS-R slope. The ALSFRS-R slope per month was also compared to a historical placebo control of the Ceftriaxone trial showing a statistical power (−0.99 vs −1.97, p=0.0047). This further analysis was specified in the FDA approved protocol.

Summary of AEs and SAEs of Phase 2A in ALS Trial

1. Safety and tolerability were evaluated based on the results of adverse events, vital signs, electrocardiography (ECG) measurements, physical and neurological examinations, safety laboratory monitoring, and hypersensitivity and injection site reactions.

2. Of all patients enrolled in the study, 9 patients reported 1 adverse event over the course of the study. Overall, in the GM604 treatment group, 5 out of 8 patients experienced at least 1 Treatment-emergent adverse events (TEAE) and 4 out of 4 patients in the placebo treatment group experienced at least 1 TEAE. No unexpected findings in the context of the known safety profile (clinical or pre-clinical) of the GM604 were observed in this study. Consistent with the protocol-defined expected adverse reactions, the most frequently reported AEs by GM604-treated patients in the present study were falls (4 patients, 50%), puncture site pain (3 patients, 37.5%), rash (2 patients) and headache (2 patients, 25%). Of these most commonly reported TEAEs in GM604-treated patients, falls (1 patient, 25%), puncture site pain (1 patient, 25%) and headache (2 patients, 50%) were reported in placebo-treated patients.

3. Adverse events in the general disorders and administration site conditions system organ class were the most frequently experienced AE (7 patients and 61 total events in both the GM604 and placebo-treated groups).

4. There was 1 serious adverse event (SAE) experienced by a patient in the GM604 treatment group. Patient 0203 who flew back to Germany experienced shortness of breath 24 days after baseline visit that required inpatient hospitalization. The investigator determined the SAE was unrelated to the investigational product.

5. No deaths or withdrawals due to adverse events occurred.

6. There were no clinically meaningful differences noted between patients who received GM604 and those who received placebo for changes over time in clinical laboratory tests, hematology parameters, or urinalysis results. There were no clinically meaningful differences noted between patients who received GM604 and those who received placebo for changes over time in ECGs, vital signs, physical findings, neurological examination, or other observations related to safety.

7. Grade 1 hypersensitivity reactions were reported by 1 patient receiving placebo treatment (Visit 2) and by 1 patient receiving GM604 treatment (Visit 5). All other patients reported an absence of hypersensitivity (Grade 0) reactions. There were no concerns regarding QT prolongation as no patient receiving treatment with GM604 had QT or QTcB result above 450 msec.

Example 4

Clinical Evaluation of GM604 for Treatment of End Stage ALS Patient

This proposed individual patient trial (GALS-C) is for compassionate use for an end stage ALS patient. The rationale is "time is brain/neurons". We hope to re-innervate the compromised motor neurons in time before their rapid progression towards death. We also want to compare how GM604 works in patients with disease onset within 2 years (Phase 2A clinical trial patients) and in an end stage ALS patient.

Case Report

GALS Compassionate Use (GALS-C) A 46 year old male ALS patient was first diagnosed with the disease in Q1 2005 and by Q3 2008 was quadriplegic and on a ventilator. The FDA approved a compassionate-use application of the MNTF6mer known as GM604 for this patient (IND #120052) using a protocol that followed the Phase 2A trial. This program was thus dubbed GALS-C.

GALS-C Study Design

1. Patient provides informed consent will be evaluated to establish baseline for clinical progression and with blood draw by IV and undergoing a lumbar puncture with an Atramatic LP needle for biomarker tests. Blood and CSF will be collected for analyzing specific protein biomakers in the CSF before drug administration. After the first LP, the 1st study dose will be given.

2. Patient will receive one 1V bolus injection once a day for three times a week during these 2 weeks for a total of six injections.

3. At the beginning of 2nd week before the 4th dose, a blood draw for Safety Labs and the 2nd blood biomarker testing will be performed.

4. After the sixth and last dose wait 60 minutes for evaluation, a blood draw for Safety Labs and the 3rd blood biomarker testing, a second lumbar puncture will be performed to test for CSF biomarkers.

5. At the 7th visit (week 6), after clinical efficacy evaluations, a blood draw for Safety Labs and the 4th blood biomarker testing will be performed.

6. At the 8th visit (Week 12), after the clinical efficacy evaluations, a blood draw for Safety Labs and the 5th blood biomarker testing and a 3rd LP will be performed.

7. All Blood and CSF samples will be collected, prepared, stored frozen at −80 C and sent for analysis together to test for biomarkers.

8. Exploratory clinical outcome measures will include the rate of decline of the ALS Functional Rating Scale Revised (ALSFRS-R), Forced Vital Capacity (FVC), stabilization or improvement in any clonus or spasticity symptoms, speech, swallowing, drooling, lingual/oral muscle, improved time off vent (self-breathing) and any movement or increase movement of any muscle groups. To estimate the participant's rate of progression prior to treatment, an ALSFRS-R of 48 will be assumed at date of symptom onset. There will be 2 weeks of active treatment, followed by 10 weeks of assessment without active treatment.

9. Plus patient will receive one booster dose every 12 weeks for three times after the initial 12 weeks.

10. At the 9th to 11th visits (Week 24, 36 and 48), after the clinical efficacy evaluations, a blood draw for Safety Labs and the 7th to 9th blood biomarker testing will be performed.

11. A 4th LP will be performed after the clinical efficacy evaluations at the 11th visit (Week 48).

12. Patient to keep detailed diary to record clinical observations.

This compassionate trial follows the similar protocol and same dosing regimen as in the Phase 2A ALS trial. 320 mg of GM604 was administered intravenously as a slow bolus, once a day for 3 times a week for 2 weeks. Patient will receive one booster dose every 12 weeks for three times after the initial 12 weeks. The patient was treated with GM604 for two weeks. After two weeks of active treatment, evaluation will be performed after the last dosing at the end of week 2 and return visits on week 6 plus evaluation on week 12, 24, 36, 48 and 60. The compassionate patient was treated for 2 weeks with six doses of 320 mg GM604 by intravenous administration and followed by 10 weeks without additional treatment. CSF and blood plasma tests and clinical evaluations were performed in various biomarkers (SOD1, Cystatin C, Tau and TDP-43).

Since the compassionate patient was very advanced, the usual clinical evaluations such as ALS functional rating scale (ALSFRS), forced vital capacity (FVC), and muscle strength were not used. The evaluation of swallowing and speech are more relevant outcomes. The sample collection of CSF by LP is difficult for the patient. The initial CSF before dosing and the CSF sample after the 6$^{th}$ dose were collected and analyzed. The PI and the drug Sponsor agreed to hold off the CSF sample draws until further notice The CSF and plasm samples collected in both the ALS Phase 2A trial (GALS-001 trial) and this compassionate trial (GASL-C) were tested and examined by Iron Horse Diagnostics. Changes were identified in specific biomarkers during GM604 treatment in ALS patients. In this case report, GALS-C measured specific biomarkers for target and efficacy. Among these biomarkers are superoxide dismutase 1 (SOD1), Cystatin C, and Tau. (Shahim P et al. 2014. Blood biomarkers for brain injury in concussed professional ice hockey players, JAMA Neurol. 71(6): 684-92; Grad L I et al. 2014. Intercellular propagated misfolding of wild-type Cu/Zn Superoxide Dismutase occurs via exosome-dependent and -independent mechanisms. Proc Nat Acad Sci USA. 111: 3620-3625; Rotunno M S et al. 2013. An Emerging Role for Misfolded Wild-type SOD1 in Sporadic ALS Pathogenesis. Front Cell Neurosci. 7:253; Wilson M E et al. 2010. Cystatin C: a candidate biomarker for amyotrophic lateral sclerosis. PLoS One. 5:e15133; Okamoto K et al. 2008. Bunina bodies in amytrophic lateral sclerosis. Neuropathology: Official Journal of the Japanese Society of Neuropathology. 28: 109-115.)

Comparison of the CSF expressions changing from baseline to end of week 2 for SOD1, Cystatin C and Tau for Compassionate use patient (GALS-C), GM 604 treated (GALS-T) and placebo treated (GALS-P) in Phase 2A are summarized in Table 5.

SOD1

SOD1 was the first gene mutation linked with ALS. This genetic mutation, of which multiple types have been identified, comprises only about 20% of genetic cases of ALS and about 2% of overall cases. However, there is growing evidence that wild-type misfolded SOD1 protein, like its genetically-mutant counterparts, is capable of assuming a form toxic to motor neurons. Moreover, misfolded wtSOD1 is capable of inducing extracellular spread of the misfolded form via a prion-like propagation mechanism SOD1 appears in increased quantity in the plasma of PALS. A single misfolded copy of this protein is sufficient to cause prion-like propagation in sporadic ALS patients. Reduction of elevated levels can control this mechanism and also indicates reduced levels of oxidative stress in the CNS SOD1 levels in ALS patient biofluids were tested as a biomarker to monitor efficacy of anti-sense oligonucleotide treatment lower SOD1 levels in animal models of ALS and human patients in early clinical trials.

The normal range of SOD1 in the CSF in healthy individuals is 50-200 ng/ml, in plasma in healthy individuals is 10-50 ng/ml. In most of the GM604 treated patients in ALS Phase 2A trial where most patients had symptom onset for less than two years, their plasma SOD1 expressions were higher than the normal range at baseline. GM604 treated patients in the Phase 2A trial had their plasma SOD1 levels reduced. The CSF SOD1 expressions at baseline in Phase 2A patients were at the higher end of normal range. At the end of two weeks, the GM604 treated patients had CSF SOD1 levels reduced from 186.6 to 153.17 (−3.75%), while the placebo group had the CSF SOD1 levels increased from 137.94 to 175.86 (+30.45%). In this advanced stage ALS patient, his CSF SOD1 level at baseline was 27.22 ng/mL, below normal. After 6 doses in two weeks, his CSF SOD1 level was 30.996 ng/mL, increased 13.84%, closer to the normal range.

Please note that GM604 can modulate the CSF SOD1 biomarkers in both directions

Cystain C

Cystatin C is a cysteine protease inhibitor widely expressed in the body. It is one of two proteins known to localize to inclusions in neuronal cytoplasm often referred to as Bunina bodies. The normal range of CSF Cystatin C in healthy subjects is 3.0-8.0 pg/ml. Cystatin C levels in the CSF of the GALS-C patient at baseline was 1.97 µg/mL, much below the normal range. After 6 dose in 2 weeks, the CSF Cystatin C level in GALS-C patient is 2.35 µg/ml, increased 19% towards the normal range. In the GALS-001trial we found that Cystatin C levels in both treated and placebo group were at the low end of the normal range. GM604 raised Cystatin C levels in the treatment group (3.11 µg/ml to 3.15 µg/ml, +1.57%) but the placebo group kept dropping (3.23 µg/ml to 3.06 µg/ml, −4.57%).

Tau

Tau has been a biomarker of neurodegeneration for many years and is extensively used for Alzheimer's disease. Tau is a protein that stabilizes microtubules. Microtubules make up the cytoskeleton necessary for axon extension and provide "roadways" for intracellular transport. Tau levels can be used to measure neuronal injury such as in the case of concussion is mainly expressed in neurons of the CNS and is crucial in axonal maintenance and transport. It is a major component of abnormal neuronal aggregates in many CNS disorders, including Alzheimer's disease (AD). High concentrations of Tau may be the results of broken microtubules and are evidence of active neuronal degeneration during early stage of neurodegenerative disease such as ALS. In advanced stage ALS patient, there is a lot less intact Microtubules to be broken to release Tau, and as a result, the Tau concentration may be low. Reducing the overall levels of this protein in patients during active stage of neural degeneration may hold therapeutic relevance. That Tau accumulation can only be reversed at an early stage in its AD pathogenesis highlights the need for therapeutic strategies to slow or even stop that accumulation. Researchers have previously used Tau as a biomarker to monitor effects of memantine treatment in ALS patients in a phase 2 clinical trial. It was shown that reduction of Tau levels in ALS patients due to drug treatment correlated to reductions of clinical parameters of ALS disease progression.

The normal range of Tau in the CSF of healthy subjects are 100-350 pg/mL. In GALS-001 trial, CSF Tau levels at baseline were at high end of normal or higher than normal. After 6 dose treatment in 2 weeks, the GM604 treated group had CSF tau level lowered (305.03 pg/ml to 303.58 pg/ml, −1.16%), while the placebo group had CSF tau level increased 386.85 pg/ml to 412.96 pg/ml, +6.43%) showing continued disease progression. In the GALS-C case, the compassionate patient is already very advanced in the disease progression, the CSF Tau level at baseline was 60.55 pg/mL, very below normal range at baseline. After 6 doses in 2 weeks, the CSF Tau level was 63.33 pg/mL, an increase of 4.59%, closer to the normal range.

The normal range of TDP 43 in plasma in healthy individual is 0-50 pg/ml. The end stage patient receiving GM604 for compassionate use had baseline TDP-43 of 144.54 pg/ml which was very high. At the end of 6 doses, it was 92.59 pg/ml and at the end of 12 weeks it was 52.53 pg/ml (almost normal). GM604 brought the TDP-43 levels towards or almost within the normal range in 12 weeks.

It was a surprise that the end stage patient's baseline TDP-43 was as high as those of the definite ALS patients within 2 years of ALS onset in phase 2A trial (mean 138.88 pg/ml at baseline). At 12 weeks, the mean of the individual placebo patients change of TDP-43 is +6%, The GM604 treated patients had change of −30%. ALS Phase 2A, slope in plasma TDP-43 through week 12 in treated (−3.513 pg/mL/wk) is lower than placebo (0.493 pg/mL/wk), p=0.0078. The TDP 43 level in the end stage patient was normalized in 12 weeks.

According to the Kyoto University research results over expressed TDP-43 spread out from the nucleus to the outside, combined and become toxic and caused the death of the other motor neurons. (Egawa N et al. 2012. Drug screening for ALS using patient-specific induced pluripotent stem cells. Sci Trans Med 4. 145ra104. TDP-43 in ALS patients has shorter axons in motor neurons than healthy subjects. When TDP-43 was decreased the death of neurons were prevented and the projection of nerves previously short became longer. Therefore the effect of the slowing down of the ALS disease progression is expected. TDP-43 is also a major disease protein found in the brains of ALS and Alzheimer patients.

Clinical Observations

The summary of the clinical observation filed with FDA by principal investigator Dr. Dawn Motyka is as follows. The clinical observation results of the GALS-C patient revealed important improvement from baseline to week 12. During the trial, no adverse side effects were noted. At week 2, patient's speech video definitely showed clearer articulation than baseline. At the end of the two weeks six-dose treatment of GM604, the patient's swallowing volume increased to 20 cc from a baseline of 10 cc. 2 weeks after the two weeks treatment, patient's swallow volume was increased 150%-200% to 25 cc-30 cc. Five weeks after treatment, the patient consumed 240 cc of water in 20-25 cc bursts without leakage. Mouth suction of water column height was increased from 5-8 cm to 10-15 cm with both ⅛ and ¼ inch straw. The increased swallow and suction ability metrics are logical in that the hypoglossal nerve is one of the shortest motor neurons in the body. The patient has also experienced improved muscle tone and increased pain in certain body parts, which was normal muscular pain in the past and had decreased after the patient had become completely paralyzed.

Biomarker data of the GALS-001 trial patients randomized to the placebo cohort all showed abnormal levels. As the trial progressed their biomarker levels continued in the abnormal direction, demonstrating that without treatment the disease will continue to uniformly become worse.

Example 5

Homeostasis

In recent ALS research, Dysfunction in RNA processing and protein homeostasis is an emerging theme. (Ling S C et al. 2013. Converging mechanisms in ALS and FTD: disrupted RNA and protein homeostasis. Neuron. 79(3): 416-438) These two processes are intimately linked, with disease-initiated perturbation of either leading to further deviation of both protein and RNA homeostasis through a feed-forward loop including cell-to-cell prion-like spread that may represent the mechanism for relentless disease progression. Therefore it can be hypothesized that a compound that can restore RNA and protein homeostasis can be a target to stop the feed-forward loop and attenuate the disease progression. The Phase 2A and compassionate use clinical studies showed that the biomarker data with GM604 can bring homeostasis, and suggested that may be how GM604 attenuate ALS disease progression. An important and unexpected aspect of the GALS-C biomarker results compared with GALS001 biomarker results is that GM604 demonstrated modulation of biomarker levels in both directions, always toward normal healthy levels. When the patient's biomarker level was below normal such as in the case of the GALS-C patient in CSF SOD1 and Tau, treatment of GM604 increased the respective biomarker level to closer to normal range. On the other hand, in the case of GALS001 trial where most ALS patient had disease onset within two years and the degeneration was active, the CSF SOD1, and Tau in both treated and placebo groups were above normal range. Treatment with GM604 reduced these biomarkers closer to normal range. Both SOD1 and Tau biomarkers in the placebo group continue to increase indicating continue disease progression. In the case of CSF Cystatin C which helps neuroprotection, the patients in GALS-C and GALS001 trial are all below or at the low end of normal range. It is desirable to raise the Cystatin C level to closer to normal range. The GALS-C patient had Cystatin C level increased by 19%, the GALS001 trial GM604 treated patients had Cystatin C level increased slightly or maintain steady, but the placebo group had Cystatins C level decreased indicating continue disease progress.

Most biomarker data in SOD1, Tau, TDP-43 for ALS patients in Phase 2A were above normal range and the GM604 treatment down regulated their expression levels. In this advance ALS patient, his data in CSF SOD1 and CSF Tau were below normal at baseline. Treatment of GM604 up regulated CSF SOD1 and CSP Tau. This surprising observation indicated that GM604 can modulate the same biomarker in both up and down regulation directions. This phenomenon is very unique, and is the hallmark of homeostasis.

Exclusion from homeostasis comparison table: The plasma level for SOD1, Tau in the End Stage patient were NOT below normal but were above normal similar to other Phase 2A patients and therefore were not used in the homeostasis comparison table to show the contrast. Plasma TDP 43 was also above normal similar to the Phase 2A patients, and was lowered from 144 pg/ml at baseline to ~50 pg/mL (normal) at week 12 similar to the other Phase 2A patients who had disease onset within two years, and therefore is also not included in the homeostasis comparison table to show the contrast.

TABLE 5

Comparison of CSF Biomarker Test Results to show HOMEOSTASIS in opposite directions
Compassionate Use (GALS-C); GALS-001 treated group (GALS-T), and placebo group (GALS-P)

| Sample-ID | SOD1 GALS-C (N = 1) ng/ml | SOD1 GALS -T (N = 8) ng/ml | SOD1 GALS-P (N = 4) ng/ml | Cystatin C GALS-C (N = 1) µg/ml | Cystatin C GALS-T (N = 8) µg/ml | Cystatin C GALS- P (N = 4) µg/ml | Total Tau GALS-C (N = 1) pg/ml | Total Tau GALS-T (N = 8) pg/ml | Total Tau GALS -P (N = 4) pg/ml |
|---|---|---|---|---|---|---|---|---|---|
| Healthy range - CSF | 50-200 | 50-200 | 50-200 | 3.0-8.0 | 3.0-8.0 | 3.0-8.0 | 100-350 | 100-350 | 100-350 |
| Baseline -CSF | 27.228 | 186.6 | 137.94 | 1.97 | 3.11 | 3.23 | 60.55 | 305.03 | 386.85 |
| Standard deviation | | 168.3 | 56.39 | | 1.35 | 0.78 | | 122.3 | 182.93 |
| Visit 6 (Week 2)-CSF | 30.996 | 153.17 | 175.86 | 2.35 | 3.15 | 3.06 | 63.33 | 303.58 | 412.96 |
| Standard deviation | | 76.14 | 84.56 | | 1.41 | 0.76 | | 139.37 | 196.62 |
| Mean % Change V6 − BL | 13.84% | −3.75% | 30.45% | 19.29% | 1.57% | −4.57% | 4.59% | −1.16% | 6.43% |

TABLE 5-continued

Comparison of CSF Biomarker Test Results to show HOMEOSTASIS in opposite directions
Compassionate Use (GALS-C); GALS-001 treated group (GALS-T), and placebo group (GALS-P)

| Sample-ID | SOD1 GALS-C (N = 1) ng/ml | SOD1 GALS-T (N = 8) ng/ml | SOD1 GALS-P (N = 4) ng/ml | Cystatin C GALS-C (N = 1) µg/ml | Cystatin C GALS-T (N = 8) µg/ml | Cystatin C GALS-P (N = 4) µg/ml | Total Tau GALS-C (N = 1) pg/ml | Total Tau GALS-T (N = 8) pg/ml | Total Tau GALS-P (N = 4) pg/ml |
|---|---|---|---|---|---|---|---|---|---|
| Standard deviation |  | 26.20% | 56.90% |  | 8.49% | 12.10% |  | 15.79% | 6.36% |
|  | below range, ↑ = DM* | high end of range, ↓ = DM* | high end of range, ↑ = DP** | below range, ↑ = DM* | low end of range, ↑ = DM* | low end of range, ↓ = DP** | below range, ↑ = DM* | high end of range, ↓ = DM* | above range, ↑ = DP** |

↑ Up regulation,
↓ Down regulation,
*DM—disease modification,
**DP = disease progression.

TDP-43. Three well known ALS biomarkers SOD1, Cystatin C and Tau were modulated by GM604 significantly towards normal range after treatment. Based on this compassionate-use study on a late stage patient, ALS biomarker expression and clinical signs were attenuated after 2 weeks of 6 doses of GM604, suggesting that GM604 might present as a potential therapeutic for ALS. The compare/contrast with the Phase 2A data is to show that GM604 regulates protein/cytokine levels both up and down, always in the direction of normal levels, as GM604 is a regulator of neuronal homeostasis.

ALS is a devastating neurodegenerative disease. It is invariably fatal with most patients dying within 3 years of diagnosis. Until recently the disease was believed to involve only the motor neurons with the cause a complete mystery. Multiple attempts to treat the disease with single-target therapies have all failed. (Ludolph A C et al. 2009. Evidence-based drug treatment in amyotrophic lateral sclerosis and upcoming clinical trials. Ther Adv Neurol Disord. 2(5): 319-326). Within the last two decades it has become clear that ALS involves multiple pathways, including factors beyond the motor neurons and outside the CNS. Even within just the motor neurons there are multiple identified pathologies occurring during ALS progression. A therapy addressing only a single one of these multiple targets is unlikely to be sufficient to arrest the disease.

Note that GM604 can modulate multiple biomarkers (Multi-target) and in both directions, the hallmark of homeostatic processes of living organisms. The inventors are pleased to report the positive result of the post hoc analysis of the homeostasis hypothesis even though there is only one patient who has the ALS disease for 10 years.

In this compassionate use study, GM604 has data that shows homeostatic effect. Not only has GM604 demonstrated statistical efficacy as shown above, but its safety profile is excellent with no significant drug related adverse events in any treatment group patients (including the inventors' trial programs for other neurodegenerative diseases).

The available data on GM604 is extremely safe and positive in metrics including: demonstrated safety, statistically-significant efficacy between treated and placebo groups in biomarker data; significant efficacy between treated and historical placebo groups in clinical data; and demonstrated ability to regulate homeostasis. For these reasons we believe that the modulations in multiple biomarkers by GM604 can be a prognostic application for ALS disease progression and the consequential clinical benefits represent a potent treatment for ALS as well as other neurodegenerative diseases.

Example 6

Figure 7:
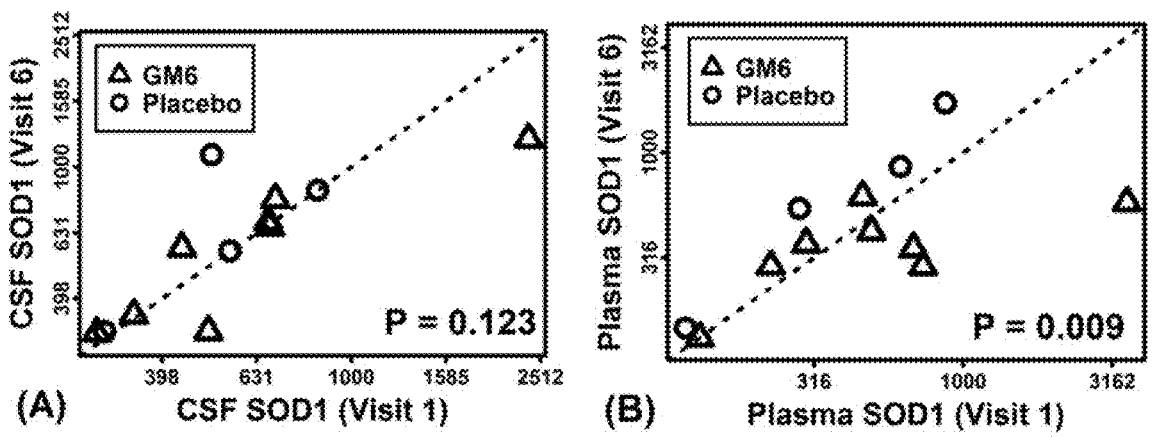
FIG. 7 shows SOD1 protein in CSF and plasma of GM6- and control-treated patients (Phase 2A clinical trial). A phase 2A trial was carried out in which 8 ALS patients were treated with GM6 and 4 ALS patients were treated with placebo. SOD1 was measured in cerebrospinal fluid (CSF) and plasma at baseline (visit 1) and following 6 doses of GM6 over 2 weeks (visit 6). In (A) and (B), each point represents a single ALS patient. Patients below the diagonal showed decreased SOD1 in CSF or plasma. P-values (lower right) were generated from a one-tailed t-test comparing change in SOD1 (visit 6-visit 1) between GM6- and placebo-treated patients.

GM604 Alters Expression of 89 Genes Associated with Amyotrophic Lateral Sclerosis in DNA Microarray Analysis DNA microarray analysis was used to analyze genes regulated by GM6 (GM604) in SH-SY5Y neuroblastoma cells. GM6-regulated genes were compared with ALS-associated genes identified from 5 database sources, yielding statistically significant overlap of GM6-regulated and ALS-associated genes in each case. By pooling results across databases, it was possible to identify 89 ALS-associated genes strongly altered by GM6 (e.g., SOD1, HIF1A, ALS2, BAX). These genes were functionally associated with motor neurons, neuron generation, neuronal death, apoptosis, and oxidative stress regulation. Consistent with the microarray findings, two weeks of GM6 treatment in ALS patients significantly reduced SOD1 protein levels in plasma (FIG. 7). These findings suggest a potential mechanism of action for GM6 in the setting of ALS, which involves SOD1 down-regulation, attenuation of oxidative stress, and activation of neuroregeneration pathways. GM6 may provide an efficacious ALS treatment option based upon a new pharmaceutical approach differing considerably from existing therapies.

The purpose of this study was to evaluate effects of GM6 on the expression of genes thought to be important for the pathogenesis of amyotrophic lateral sclerosis (ALS). DNA microarray analysis was used to identify genes altered by 48 hours of GM6 treatment in SH-SY5Y neuroblastoma cells. Based upon these data, expression shifts of ALS-associated genes following GM6 treatment were evaluated. Normalization, data processing and differential expression analysis methods were consistent with previous reports. The definition of an "ALS-associated" gene varies according to database sources, with different sources applying alternative criteria and varying levels of stringency. This study therefore utilized five alternative database sources to identify ALS-associated genes: (1) ALS Online Genetics Database (ALSoD); (2) NHGRI-EBI GWAS Catalog; (3) Online Mendelian Inheritance in Man (OMIM); (4) DisGeNET database: and (5) Medical Subject Headings (MeSH) database.

Each database was used to identify ALS-associated genes, and such genes were evaluated to determine how expression was altered by GM6. Although the pathogenesis of ALS is not completely understood, it is reasonable to expect that ALS-associated genes from databases cited above would be related to pathways and signaling cascades mediating the disease process. It was therefore hypothesized that such genes would exhibit unique expression responses to GM6, either being disproportionately increased or decreased by GM6 treatment. Gene set enrichment analysis was therefore performed to determine if ALS-associated genes were more strongly altered by GM6 treatment, as compared to all other protein-coding genes with detectable expression in SH-SY5Y cells. Analysis of Gene Ontology (GO) biological process (BP) terms was then performed to characterize functional characteristics of the ALS-associated genes altered by GM6. These analyses were repeated with respect to each of the five data sources cited above. In this report, unless otherwise indicated, GM6-increased genes are defined as those being altered by GM6 with fold-change greater than 1 (GM6/CTL; FDR<0.10), while GM6-decreased genes are defined as those altered by GM6 with fold-change less than 1 (GM6/CTL; FDR<0.10). Table 6 below shows 13452 genes with detectable expression were categorized based upon the degree to which expression was altered by GM6.

TABLE 6

| | |
|---|---:|
| Strong increase (FDR < 0.10, FC > 2.00) | 581 genes |
| Mild increase (FDR < 0.10, FC > 1.50) | 1418 genes |
| Weak increase (FDR < 0.10, FC > 1.00) | 1600 genes |
| Strong decrease (FDR < 0.10, FC < 0.50) | 678 genes |
| Mild decrease (FDR < 0.10, FC < 0.67) | 789 genes |
| Weak decrease (FDR < 0.10, FC < 1.00) | 998 genes |
| No change (FDR > 0.10) | 7388 genes |

Tables 7-10 additionally categorize GM6-regulated genes based upon fold-change thresholds of varying stringency (i.e., weak, moderate, or strong changes in gene expression).

Figure 6:
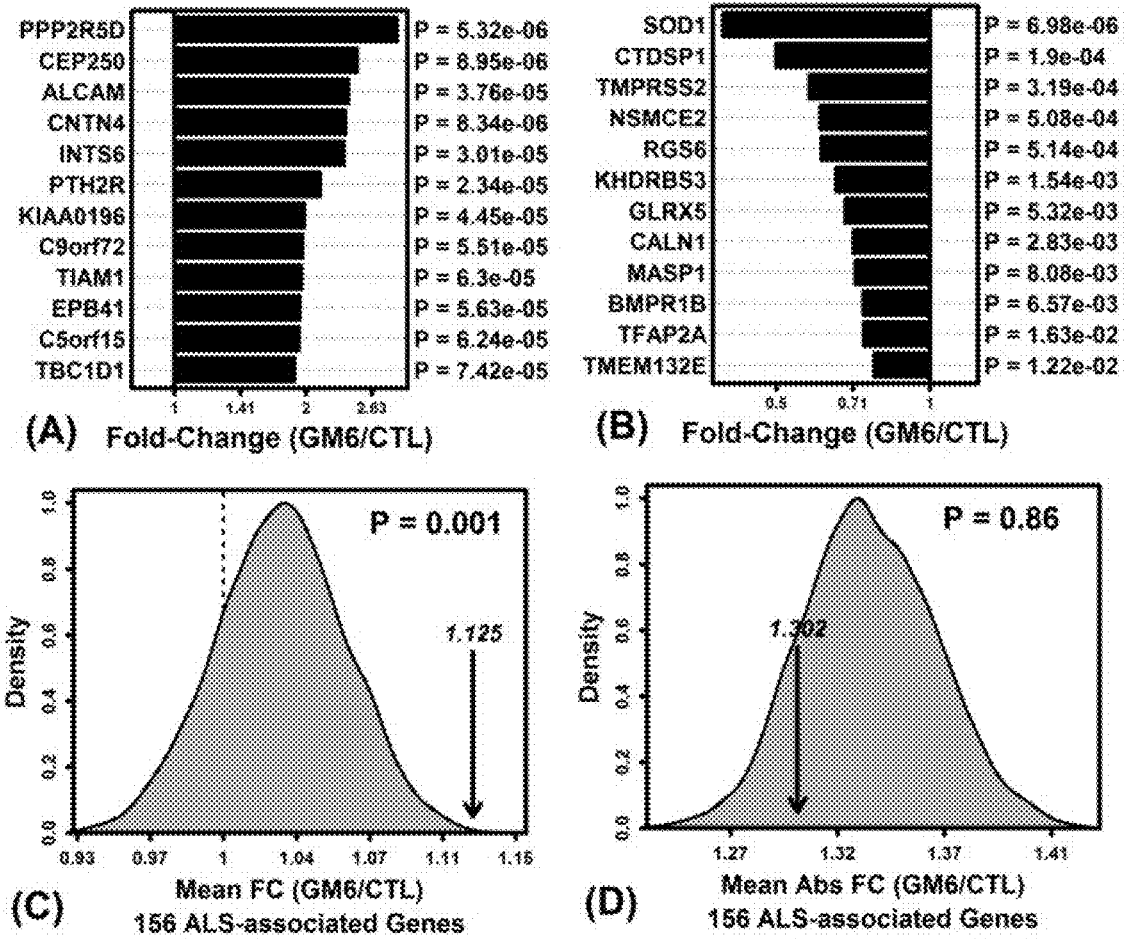
FIG. 6. Shows genes associated with ALS in GWAS studies and their response to GM6 in SH-SY5Y cells. 6 (A) shows ALS-associated genes most strongly increased by GM6. 6 (B) shows ALS-associated genes most strongly decreased by GM6.

The NHGRI-EBI GWAS catalog provides curation of genes associated with human traits and diseases through genome-wide association studies (GWASs) (https://www.ebi.ac.uk/gwas/: PMID: 24316577). The most recent version of the NHGRI-EBI GWAS catalog was used for the current analysis (released Sep. 27, 2016). From this source, 156 ALS-associated genes expressed by SH-SY5Y cells were identified as shown in FIG. 6 (49 GM6-increased; 19 GM6-decreased; Table 2). These genes were associated with the NHGRI-EBI traits "Amyotrophic lateral sclerosis", "Amyotrophic lateral sclerosis (age of onset)", and "Amyotrophic lateral sclerosis (sporadic)".

The ALS-associated genes most strongly increased by GM6 included protein phosphatase 2 regulatory subunit B'delta (PPP2R5D), centrosomal protein 250 (CEP250), and activated leukocyte cell adhesion molecule (ALCAM) (Figure A below). ALS-associated genes most strongly decreased by GM6 included superoxide dismutase 1 (SOD1), CTD small phosphatase 1 (CTDSP1) and transmembrane protease serine 2 (TMPRSS2). As a group, the 156 ALS-associated genes were more likely to be increased by GM6 as compared to other protein-coding genes expressed by SH-SY5Y cells (P=0.002). On average, GM6 increased the 156 ALS-associated genes by 12.5%, which is significantly greater than observed among randomly sampled sets of 156 genes. The average change in GM6 expression was 30.2% (increased or decreased), but this was not significantly greater than other protein-coding genes (P=0.152). Table 7 (below) shows ALS-associated genes identified from multiple database sources exhibit unique expression responses to GM6 in SH-SY5Y cells. *Directional test. P<0.05$^\dagger$ indicates that ALS-associated genes were more likely to be increased by GM6 as compared to all other genes expressed by SH-SY5Y cells (n=5000 simulation trials). **Non-directional test. P<0.05$^\dagger$ indicates that ALS-associated genes were more likely to be altered (increased or decreased) by GM6 as compared to all other genes expressed by SH-SY5Y cells (5000 simulation trials).

TABLE 7

Table 7. ALS-associated genes identified from multiple database sources exhibit unique expression responses to GM6 in SH-SY5Y cells. *

| Source | ALS Genes | GM6 ▲ | GM6 ▼ | Test 1* | Test 2** |
|---|---:|---:|---:|---|---|
| ALSoD | 78 | 35 | 8 | P = 0.004$^\dagger$ | P = 0.152 |
| GWAS Catalog | 156 | 49 | 19 | P = 0.002$^\dagger$ | P = 0.859 |
| OMIM | 21 | 14 | 1 | P = 0.001$^\dagger$ | P = 0.04$^\dagger$ |
| DisGeNET | 198 | 61 | 37 | P = 0.304 | P = 0.003$^\dagger$ |
| MeSH | 609 | 178 | 125 | P = 0.184 | P = 0.003$^\dagger$ |

The 49 GM6-increased ALS-associated genes were associated with cell projection organization, cell morphogenesis, neuron cell-cell adhesion, neurogenesis, and the toll-like receptor signaling pathway (data not shown). Online Mendelian Inheritance in Man (OMIM) is a catalog of human genes and their associations with traits and genetic disorders (http://www.omim.org/). This data source applies stringent criteria to identify ALS-associated genes, based upon documented associations between genes and phenotypes. From this database, it was possible to identify 21 ALS-associated genes expressed by SH-SY5Y cells (14 GM6-increased; 1 GM6-decreased; Table 7). ALS-associated genes most strongly increased by GM6 included alsin Rho guanine nucleotide exchange factor (ALS2). TANK binding kinase 1 (TBK1) and matrin 3 (MATR3). ALS-associated genes most strongly decreased by GM6 included superoxide dismutase 1 (SOD1), sequestosome 1 (SQSTM1) and optineurin (OPTN).

As a group, the 21 ALS-associated genes were more likely to be increased by GM6 as compared to other protein-coding genes expressed by SH-SY5Y cells (P=0.001; Figure C below). On average, GM6 increased the 156 ALS-associated genes by 36.9%, which is significantly greater than observed among randomly sampled sets of 156 genes. The average change in GM6 expression was 49.6% (increased or decreased), which was significantly greater than other protein-coding genes (P=0.04; Figure D below). The 21 ALS-associated genes were therefore more responsive to GM6 than observed among randomly sampled sets of 21 genes. (data not shown).

DisGeNET is a recently developed resource that catalogues associations between genes and human diseases (http://www.disgenet.org/web/DisGeNET/menu; PMID: 25877637). This is a comprehensive database that "pools" information from a variety of sources, including CTD, UniProt, the Rat Genome Database, the Mouse Genome Database, published GWAS studies, and information derived by text mining of the Entrez GeneRIF database and MEDLINE abstracts. The DisGeNET database was used to identify 198 ALS-associated genes (61 GM6-increased; 37 GM6-decreased). It would have been possible to identify as many as 799 ALS-associated genes using DisGeNET. However, as an additional filter, the current analysis is limited to genes associated with ALS with respect to at least two PubMed publications. ALS-associated genes most strongly increased by GM6 included presenilin 1 (PSEN1), fibroblast growth factor 2 (FGF2), and alsin Rho guanine nucleotide exchange factor (ALS2) (see A below). ALS-associated genes most strongly decreased by GM6 included KH-type splicing regulatory protein (KHSRP), insulin (INS) and cystatin C (CST3) (see B below).

As a group, the 198 ALS-associated genes were increased by 4.2% on average following GM6 treatment, which was not significantly different compared to other genes. However, the 198 ALS-associated genes were, on average, altered by 40.5% on average (increased or decreased), which was significantly larger than all other protein-coding genes expressed by SH-SY5Y cells (P=0.003). The 198 ALS-associated genes were therefore more responsive to GM6 than observed among randomly sampled sets of 198 genes. The 61 GM6-increased ALS-associated genes were associated with response to oxidative stress, generation of neurons, neuron projection morphogenesis, negative regulation of neuron death and response to unfolded protein. The 37 GM6-decreased ALS-associated were associated with death, development of female sexual characteristics, response to oxidative stress, response to axon injury and negative regulation of neuron apoptotic process (data not shown).

Figure 8:
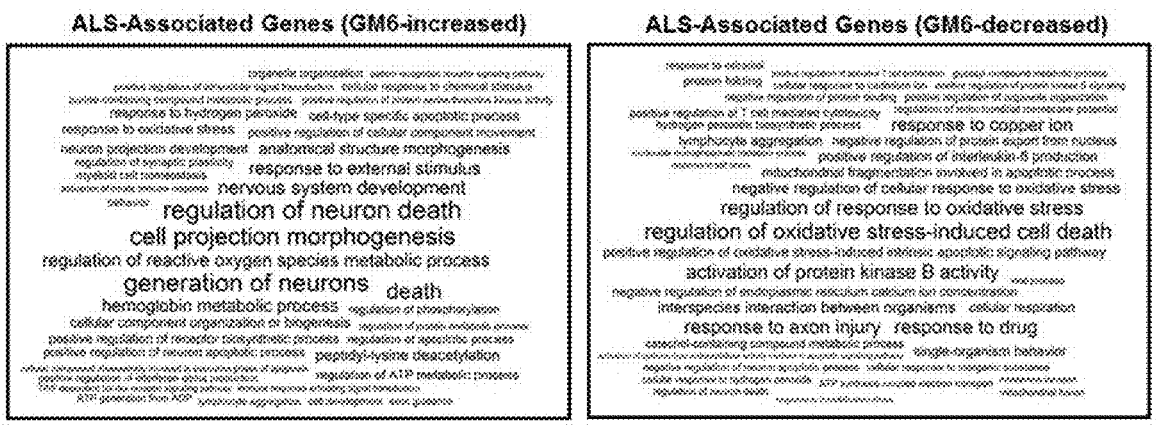
FIG. 8 shows functional associations of ALS-associated genes altered by GM6. Gene ontology (GO) biological process (BP) terms enriched among the 43 ALS-associated GM6-increased genes (left) and 46 ALS-associated GM6-decreased genes (right) are shown. Larger font sizes indicate more statistically significant association between the GO BP term and the set of ALS-associated genes (conditional hypergeometric test).

These results are consistent with the idea that GM6 alters cellular signaling pathways involved in the pathogenesis of ALS. The ALS-associated genes identified in this report provide candidates for further studies to elucidate mechanisms by which GM6 may promote motor neuron survival in ALS patients. Such genes may also provide clinical biomarkers that could be applied in clinical studies of human participants. Overall, combining results across all data sources, it was possible to identify 43 ALS-associated genes strongly increased by GM6 (FDR<0.10 with FC>2.0), along with 46 ALS-associated genes strongly decreased by GM6 (FDR<0.10 with FC<0.50). These genes are summarized in the table below and provide candidates for understanding mechanisms by which GM6 may influence pathways mediating ALS pathogenesis. Table 8 (below) shows 89 ALS-associated genes strongly altered by GM6. Biological processes most strongly associated with these gene sets are represented in the word clouds in FIG. 8.

TABLE 8

Table 8. 89 ALS-associated genes strongly altered by GM6. Genes were associated with ALS by at least 1 of 5 database sources (see Table 7). Genes are ranked such that the first genes listed were most strongly altered by GM6 (e.g., MAT2A and NPY).

| | |
|---|---|
| ALS-associated genes strongly increased by GM6 (FDR < 0.10, FC > 2.00) | MAT2A, OSBP, HIF1A, UBAP2L, PPP2R5D, CNTN4, DNM1L, FGF2, CEP250, HSPD1, PAK1, DPYSL3, ADAM10, PSEN1, SMC3, FOXO3, ADD1, TBK1, ALS2, TNPO1, HUS1, HDAC4, PTH2R, DAG1, MFN1, RBMS3, INTS6, CAT, DCTN1, HDAC6, ALCAM, LIG4, SS18L1, SPAST, SLC18A3, ATP2B2, MAP3K7, MATR3, CASP3, DCTN5, SQLE, TCP1, BRAP |
| ALS-associated genes strongly decreased by GM6 (FDR < 0.10, FC < 0.50) | NPY, PARK7, RCC1, ARHGAP18, PFDN2, TXN, PPIH, CST3, NES, PFDN5, NPEPPS, TAF15, FIS1, APRT, NDUFA2, SOD1, BAX, INS, CREBBP, LAGE3, EXOSC1, SUMO3, B2M, CYP1A2, GAP43, LGALS1, NRGN, FADD, DDIT3, EIF3K, GSTO1, KHSRP, SRP14, POLR2H, LY6E, PABPN1, PNO1, IGFBP2, NDUFB3, CTDSP1, S100A6, KIN, RAB5A, TH, SNCG, CD163 |

Of the 89 ALS-associated genes strongly altered by GM6, 11 were associated with the Gene Ontology term "regulation of neuron death" (GO:1901214) (PARK7, NES, HIF1A, SOD1, BAX, HSPD1, PSEN1, FOXO3. TBK1, HDAC4, DDIT3, LIG4, CASP3). Additionally, 24 of 89 were associated with the Gene Ontology term "generation of neurons" (GO:0048699) (NPY, HIF1A, SOD1, CNTN4, FGP2, BAX, PAK1, DPYSL3, ADAM10, PSEN1, ALS2, DAG1, GAP43, LGALS1, ALCAM, LIG4, SS18L1, SPAST, ATP2B2, CASP3, CTDSP1, S100A6, BRAP, TH). The majority of the 89 genes (71 of 89) were linked to the Medical Subject Headings (MESH term) "apoptosis" (D017209) via specific PubMed publications (e.g., MAT2A, NPY, PARK7, RCC1, ARHGAP18). Likewise, 21 of 89 were linked to the MESH anatomy term "Motor Neurons" (D009046) via articles included within the PubMed database (PARK7, CST3, TAF15, SOD1, FGF2, BAX, CREBBP, DPYSL3, ALS2, HDAC4, DCTN1, HDAC6, DDIT3, SS18L1, PABPN1, SPAST, SLC18A3, CASP3, TCP1, S100A6, SNCG).

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features reported and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treatment for amyotrophic lateral sclerosis (ALS), the method comprising the steps of:
   i) selecting a subject,
   ii) quantifying a biomarker for ALS in said subject, wherein the biomarker is selected from the group consisting of TDP-43, SOD1, and Tau,
   iii) classifying the subject as in need of treatment for ALS, when the quantity of said biomarker is above normal for a healthy subject, and
   iv) treating the subject for ALS, wherein the treating comprises administering a MNTF peptide consisting of the amino acid sequence FSRYAR [SEQ ID NO:2] (GM604) to the subject.

2. A method according to claim 1, wherein said quantifying comprises measuring the mRNA amount or expression levels of one or more biomarkers.

3. A method according to claim 1, wherein said quantifying comprises measuring the protein expression levels of one or more biomarkers.

4. A method according to claim 1, wherein said quantity of biomarker is above a normal range for a healthy subject is 50 pg/ml plasma of TDP-43; 200 ng/ml cerebrospinal fluid (CSF) or 50 ng/ml plasma of SOD1; and 350 pg/ml CSF of Tau.

5. The method of claim 1, wherein the quantity of the biomarker is an increase of 10% above normal for a healthy subject.

6. The method of claim 1, wherein the quantity of the biomarker is an increase of 20% above normal for a healthy subject.

7. The method of claim 1, wherein the quantity of the biomarker is an increase of 30% above normal for a healthy subject.

8. A method according to claim 4, wherein said biomarker is TDP-43.

9. A method according to claim 1, wherein the biomarker is Tau.

10. A method according to claim 1, wherein the biomarker is SOD1.

11. A method according to claim 1, the method further comprising repeating the quantifying of the biomarker after treating said selected subject for ALS.

12. The method of claim 11, wherein the further treatment of the subject with the peptide of SEQ ID NO: 2 is either increased or decreased to bring the level of the biomarker towards or within the normal range for a healthy subject.

13. A method according to claim 1, wherein the biomarker is down-regulated in response to the treatment of step iv).

14. A method according to claim 13, wherein the biomarker down-regulated in response to the treatment is selected from the group consisting of TDP-43 and SOD1.

15. A method according to claim 1, further comprising quantifying an additional biomarker selected from the group consisting of Cystatin-C, IRS1, IRS2, AKT1, PIK3, and C9orf72.

16. A method according to claim 15, wherein said quantity of additional biomarker is below a normal range for the biomarker in a healthy subject.

17. A method according to claim 15, wherein the classifying of step iii) occurs when the quantity of the additional biomarker is below normal for a healthy subject, and the additional biomarker is up-regulated in response to the treatment of step iv).

18. A method according to claim 17, wherein the additional biomarker up-regulated in response to the treatment is Cystatin-C.

* * * * *